(12) United States Patent
Johnstone et al.

(10) Patent No.: US 7,355,047 B2
(45) Date of Patent: Apr. 8, 2008

(54) SUBSTITUTED QUINOLONE CARBOXYLIC ACIDS, THEIR DERIVATIVES, SITE OF ACTION, AND USES THEREOF

(75) Inventors: Timothy B. C. Johnstone, Costa Mesa, CA (US); Derk J. Hogenkamp, Carlsbad, CA (US); Kelvin W. Gee, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 103 days.

(21) Appl. No.: 10/514,808

(22) PCT Filed: May 12, 2003

(86) PCT No.: PCT/US03/14948

§ 371 (c)(1),
(2), (4) Date: Nov. 12, 2004

(87) PCT Pub. No.: WO03/097564

PCT Pub. Date: Nov. 27, 2003

(65) Prior Publication Data

US 2006/0178516 A1    Aug. 10, 2006

Related U.S. Application Data

(60) Provisional application No. 60/380,641, filed on May 14, 2002.

(51) Int. Cl.
*C07D 215/38*    (2006.01)
*C07D 215/46*    (2006.01)

(52) U.S. Cl. ............... 546/156; 514/220; 514/250; 514/312

(58) Field of Classification Search ............... 514/220, 514/250, 312; 546/156
See application file for complete search history.

(56) References Cited

U.S. PATENT DOCUMENTS

| 4,390,541 A | 6/1983 | Goldsworthy et al. |
| 6,248,739 B1 * | 6/2001 | Turner et al. ............ 514/235.2 |
| 6,413,956 B1 * | 7/2002 | Albaugh et al. ............ 514/220 |

FOREIGN PATENT DOCUMENTS

| EP | 0 055 068 A1 | 6/1982 |
| WO | WO 00/68202 A1 | 11/2000 |

OTHER PUBLICATIONS

Piganeau, J Mol Biol, vol. 312, pp. 1177-1190, 2001.*
Kalkote, Tetrahedron Letters, vol. 37, No. 37, pp. 6785-6786, 1996.*
Uno, Toshio et al. "Synthesis of Antimictobial Agents. I. Syntheses and Antribacterial Activities of 7-(Azole substituted) quinolones" Journal of Medicinal Chemistry. Dec. 1987, vol. 30, No. 12, pp. 2163-2169.

* cited by examiner

*Primary Examiner*—D. Margaret Seaman
(74) *Attorney, Agent, or Firm*—Heller Ehrman LLP

(57) ABSTRACT

Substituted quinolone carboxylic acids and their derivatives are described. These compounds modulate the effect of γ-aminobutyric acid (GABA) via a novel site on the $GABA_A$ receptor complex in a therapeutically relevant fashion and may be used to ameliorate CNS disorders amenable to modulation of the $GABA_A$ receptor complex.

14 Claims, 14 Drawing Sheets

SUBSTITUTED QUINOLONE CARBOXYLIC ACIDS, THEIR DERIVATIVES, SITE OF ACTION, AND USES THEREOF

RELATED APPLICATION

This application claims priority to U.S. provisional application Ser. No. 60/380,641, filed on May 14, 2002.

FIELD OF THE INVENTION

This invention is in the field of medicinal chemistry. In particular, the invention relates to substituted quinolone carboxylic acids and their derivatives, which modulate, via a unique site, the effect of γ-aminobutyric acid (GABA) on the $GABA_A$ receptor complex in a therapeutically relevant fashion and may be used to ameliorate CNS disorders amenable to modulation of the $GABA_A$ receptor complex.

BACKGROUND OF THE INVENTION

GABA is the most abundant inhibitory neurotransmitter in the mammalian brain. GABA controls brain excitability by exerting inhibitory functions on neuronal membranes by altering their permeability to specific ions. Binding of GABA to the $GABA_A$-type ($GABA_A$) receptor increases the permeability of neuronal membranes to chloride ions (Cl—). In most neurons the relative Cl— ion concentration is greater outside than the inside the membrane. Thus, selective permeability to Cl— initiated by GABA binding allows Cl— to flow down its electrochemical gradient into the cell. The majority of fast inhibitory synaptic transmission is a result of GABA binding to the $GABA_A$ receptors. $GABA_A$ receptors are ubiquitously expressed throughout the CNS with almost all neurons staining for their presence. The $GABA_A$ receptor is a hetero-pentameric protein structure of the nicotinic acetylcholine receptor superfamily. Native $GABA_A$ receptors are formed from at least 19 related subunits. The subunits are grouped into α, β, δ, ε, π, and ρ families. The most prevalent combination of $GABA_A$ receptors is a stoichiometric combination of the 2×α, 2×β, and 1×γ subunits, with the remaining subunits relegated to substituting for the γ subunit during specific development expression or in highly specific brain region localization. The adult brain predominately express the α1β2γ2 subunit combination (60%) with the α2β3γ2 and α3βnγ2 subunits comprising the majority (35%) of the remaining receptors. The relative effects of GABA are influenced by the $GABA_A$ receptor subunit expressed in a specific brain region or neuronal circuit.

The neurophysiological effects of GABA result from a conformational change that occurs when GABA binds to the $GABA_A$ receptor. The $GABA_A$ receptor and the associated ion channel complex (GRC) is a ligand-gated ion channel which recognizes many compounds that allosterically modulate the ability of GABA to bind to the $GABA_A$ receptor. The allosteric modulators have distinct sites on the GRC. These sites are separate and unique from the site that recognizes GABA. The most widely studied and characterized class of allosteric modulator of the GRC is that which interact with the benzodiazepine (BZ)-site.

Alternative sites for modulating the GRC have been described. For example, neuroactive steroids are non-hormonal steroids that bind and functionally modulate the GRC. The current role of neuroactive steroids in $GABA_A$ receptor pharmacology is supported by overwhelming evidence. Electrophysiological and biochemical techniques have confirmed the capacity of neuroactive steroids to allosterically modulate the GRC through a unique site of action. Experimentally neuroactive steroids exhibit a pharmacological profile similar, but not identical, to the benzodiazepines. Neuroactive steroids produce anxiolytic, anti-convulsant, and sedative-hypnotic properties.

Certain antibacterial fluoroquinolone antibiotics have been implicated in clinical reports as the cause of convulsions in humans (Ball P (1986) *Journal of Antimicrobial Chemotherapy.* 18 Suppl D 187-193; Simpson K J, Brodie M J (1985) *Lancet ii:* 161, 1985; Hori S, et al. (1 987) *Program and Abstracts of the Twenty-Seventh Interscience Conference on Antimicrobial Agents and Chemotherapy,* New York 1987. Abstract 30, pg 101). Experimentally, fluoroquinolones have been demonstrated to produce convulsions and death in mice. Additionally, non-steroidal anti-inflammatory drugs (NSAIDs) and their by-products have been reported to clinically and experimentally potentiate the convulsive effects of the fluoroquinolones. Concerns about the convulsant side-effects of fluoroquinolone antibacterial agents have led to an interest in the interaction of fluoroquinolones with the $GABA_A$ receptor. Convincing evidence has accumulated that suggests that they interact with the GRC to inhibit GABA action. Fluoroquinolones antagonize [$^3$H]muscimol and [$^3$H]GABA binding to the GRC with high micromolar potency. Electrophysiological studies have demonstrated that fluoroquinolones alone weakly reduce GABA-evoked currents. As well, radioligand binding assays have shown that fluoroquinolones, in combination with NSAEDs, induce a conformational change in the $GABA_A$ receptor-chloride channel complex that is indicative of a pharmacologically relevant response consistent with functional antagonism of GABA.

It is well-documented that modulation of the GRC can ameliorate anxiety, seizure activity, and insomnia. Thus, GABA and drugs that act like GABA or facilitate the effects of GABA (e.g., the therapeutically useful barbiturates and benzodiazepines (BZs) such as Valium) produce their therapeutically useful effects by interacting with specific modulatory sites on the GRC. None of the known drugs, however, are selectively potent at the α-2 subunit of the GABA receptor. Thus, they exhibit undesirable side effects of sedation, and in the case of fluoroquinolones, convulsions. There is presently a need for GRC modulators that are active without side effects.

SUMMARY OF THE INVENTION

The present invention relates to molecules that modulate the GRC with selective potency at the α-2 subunit of GABA to produce therapeutically useful effects without side effects. The present invention further relates to substituted quinolones represented by Formula I that act as enhancers of GABA-facilitated Cl⁻ flux mediated through the $GABA_A$ receptor complex (GRC).

The invention also relates to methods of treating disorders responsive to enhancement of GABA action on GABA receptors in a mammal by administering an effective amount of a compound of Formula I and by activation of the novel site which mediates the action of a compound of Formula I as described herein. The novel site is defined by exclusion criteria where a compound of Formula I does not act on known sites of the GRC which include the sites for GABA, benzodiazepines, neuroactive steroids, t-butylbicyclophosphorothionate/picrotoxin, barbiturates, 4'-chlorodiazepam, antibacterial quinolones, ivermectin, loreclezole/mefanamic acid, furosemide and propofol (E. R. Korpi, G. Grunder, H. Luddens, *Progress Neurobiology* 67:113-159, 2002).

The compounds of the present invention, being ligands for a unique site on the GRC, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; acute and chronic pain; cognitive disorders; insomnia; migraine; and depressive or bipolar disorders, for example single-episode or recurrent major depressive disorder, dysthymic disorder, bipolar I and bipolar II manic disorders, and cyclothymic disorder.

Another aspect of the present invention is directed to the use of the site that mediates the activity of compounds of Formula I as enhancers or inhibitors of GABA-facilitated Cl$^-$ conductance mediated through the GABA$_A$ receptor complex. Enhancement of GABA-mediated chloride conductance is useful for the treatment and prevention of such disorders as anxiety and stress related disorders, depression and other affective disorders, epilepsy and other seizure disorders, insomnia and related sleep disorders, and acute and chronic pain. Inhibition of GABA-mediated chloride conductance is useful for the treatment and prevention of disorders related to learning and memory such as mild cognitive impairment, age related cognitive decline, senile dementia, Alzhiemer's disease, sleep disorders involving reduced wakefulness such as narcolepsy and idiopathic hypersomnia.

Also, an aspect of the present invention is to provide a pharmaceutical composition useful for treating disorders responsive to the enhancement GABA-facilitated Cl$^-$ flux mediated through the GRC, containing an effective amount of a compound of Formula I in a mixture with one or more pharmaceutically acceptable carriers or diluents.

Compounds useful in the present invention have not been heretofore reported. Thus, the present invention is also directed to novel substituted quinolones having the structure of Formula I.

Further, the present invention is directed to $^3$H, $^{35}$S, $^{36}$Cl, $^{125}$I, $^{131}$I and $^{14}$C radiolabeled compounds of Formula I and their use as a radioligand for their binding site on the GRC.

Additional embodiments and advantages of the invention will be set forth in part in the description that follows, and in part will be obvious from the description, or may be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

Figure 1:
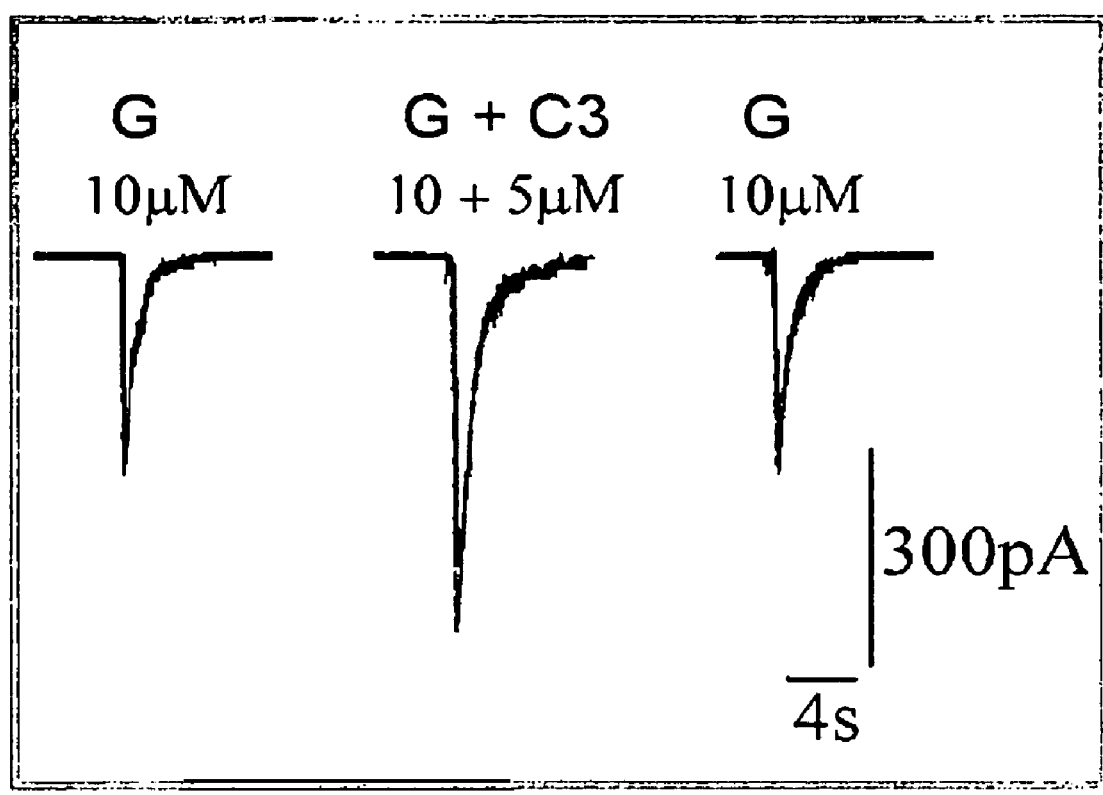
FIG. 1 depicts the potentiating effect of 7-chloro-1-ethyl-6-(1,2,3,4-tetrahydronaphthyl-1-amino)-4-oxo-1,4-dihydro-quinoline-3-carboxylic acid (C3, 5 μM) on GABA (G, 10 μM) induced chloride currents in embryonic rat hippocampal neurons. These data demonstrate that C3 is a positive efficacy modulator of GABA-gated chloride channels.
Figure 2:
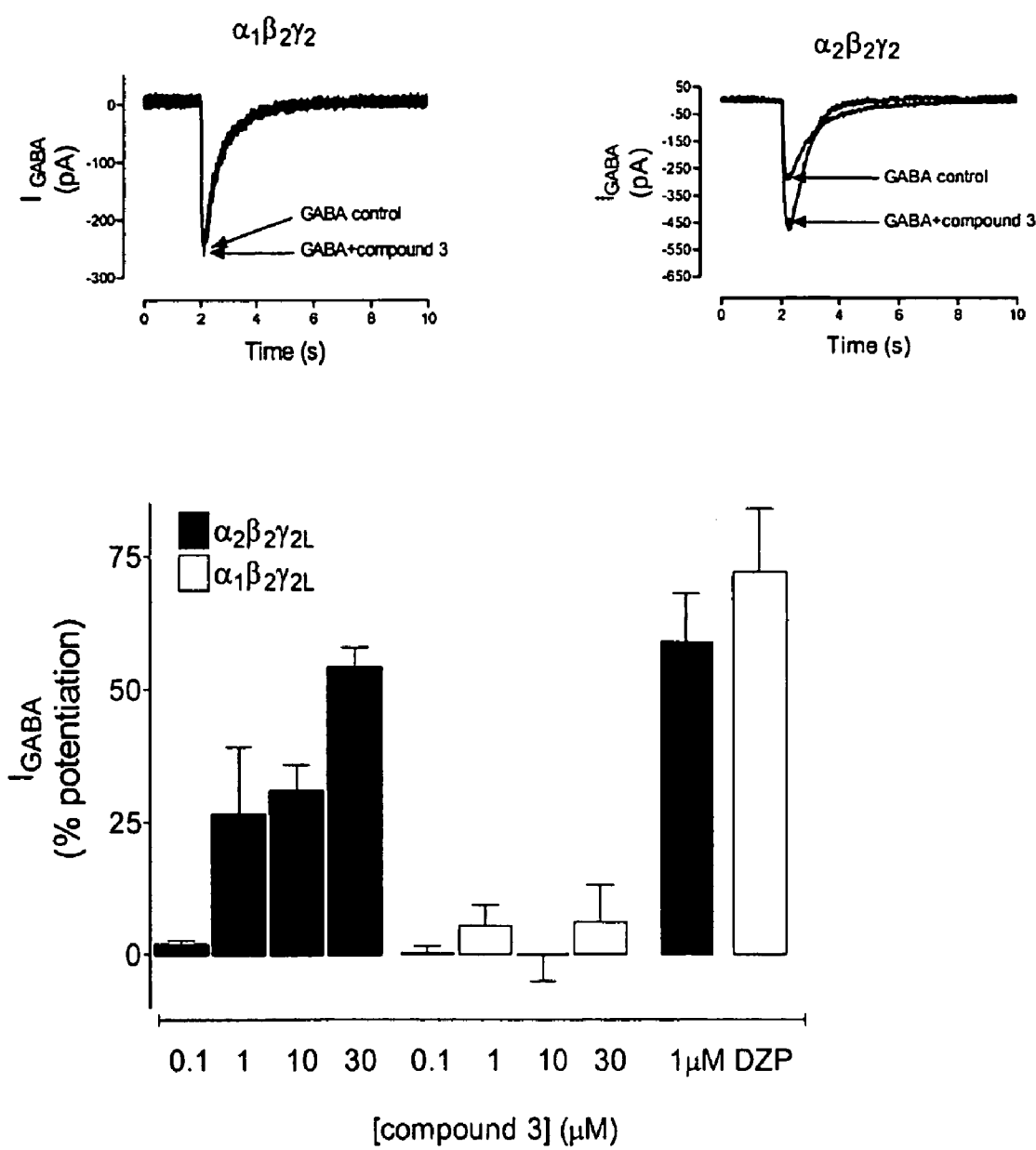
FIG. 2 depicts receptor subunit selectivity and dose-dependent positive efficacy of 7-chloro-1-ethyl-6-(1,2,3,4-tetrahydro-naphthyl-1-amino)-4-oxo-1,4-dihydroquinoline-3-carboxylic acid (compound 3, CMP 3) versus diazepam (DZP) on GABA induced currents ($I_{GABA}$) in expressed human GABA$_A$ receptors containing $\alpha_1\beta_2\gamma_2$ versus $\alpha_2\beta_2\gamma_2$ subunits.
Figure 3:
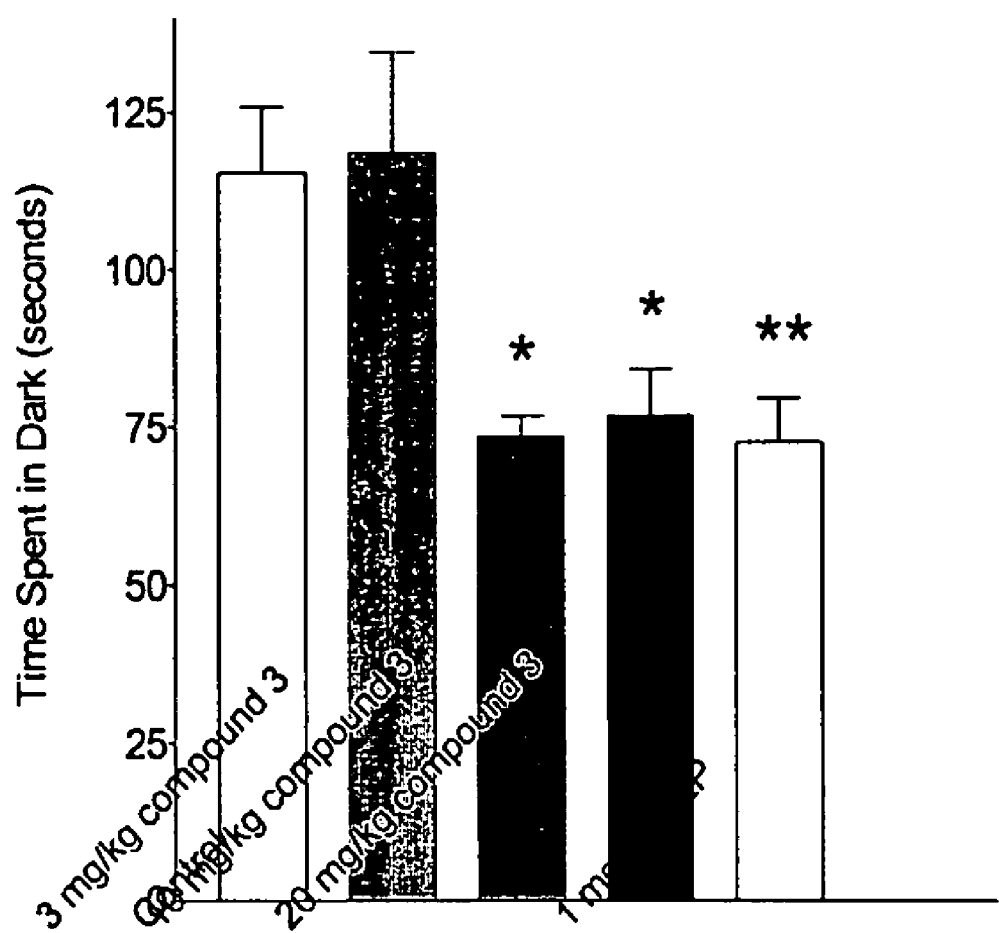
FIG. 3 depicts a comparison of 7-chloro-1-ethyl-6-(1,2,3,4-tetrahydronaphthyl-1-amino)-4-oxo-1,4-dihydroquinoline-3-carboxylic acid (compound 3) and Diazepam (DZP) on time spent in the dark in the Mouse Light-Dark Transition Model of Anxiety. These data demonstrate that the anti-anxiety effects, as shown by the increase in the time spent in the dark, of compound 3 are comparable to that of DZP.
Figure 4:
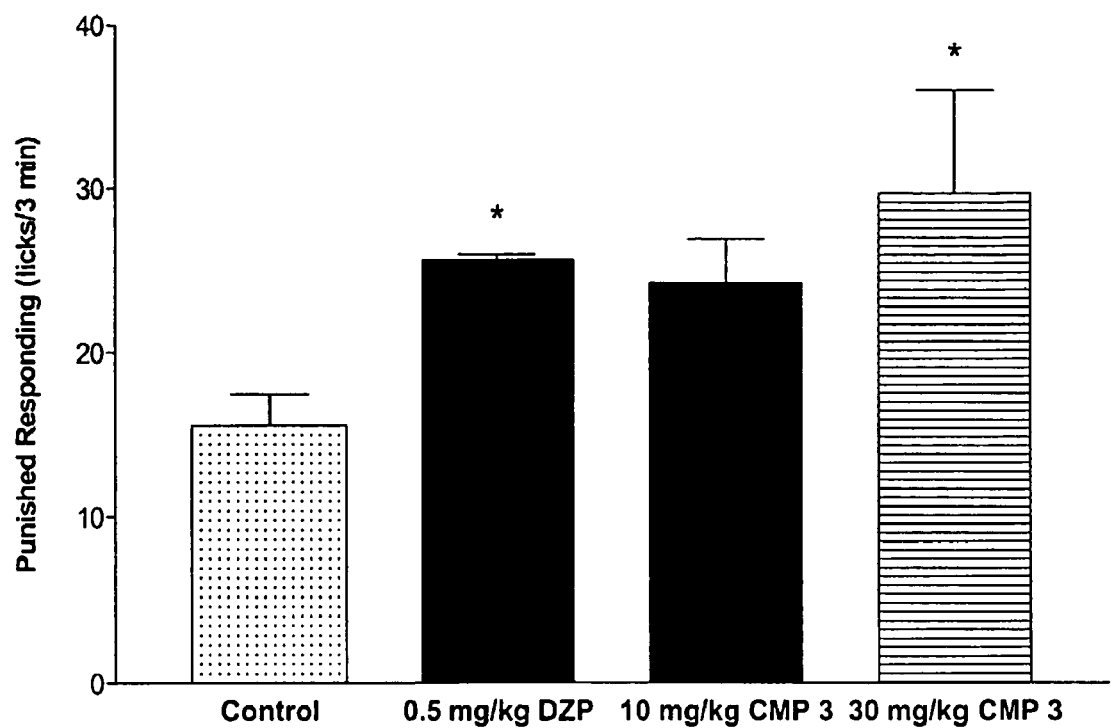
FIG. 4 depicts a comparison of 7-chloro-1-ethyl-6-(1,2,3,4-tetrahydronaphthyl-1-amino)-4-oxo-1,4-dihydroquinoline-3-carboxylic acid (CMP 3) and Diazepam (DZP) on punished responding as measured by the number of licks during a 3 minute period in the Vogel Model of Anxiety using 24 hour thirsted rats. These data demonstrate that the anti-anxiety effects, as shown by increased punished licking, of compound 3 are comparable to that of DZP.
Figure 5:
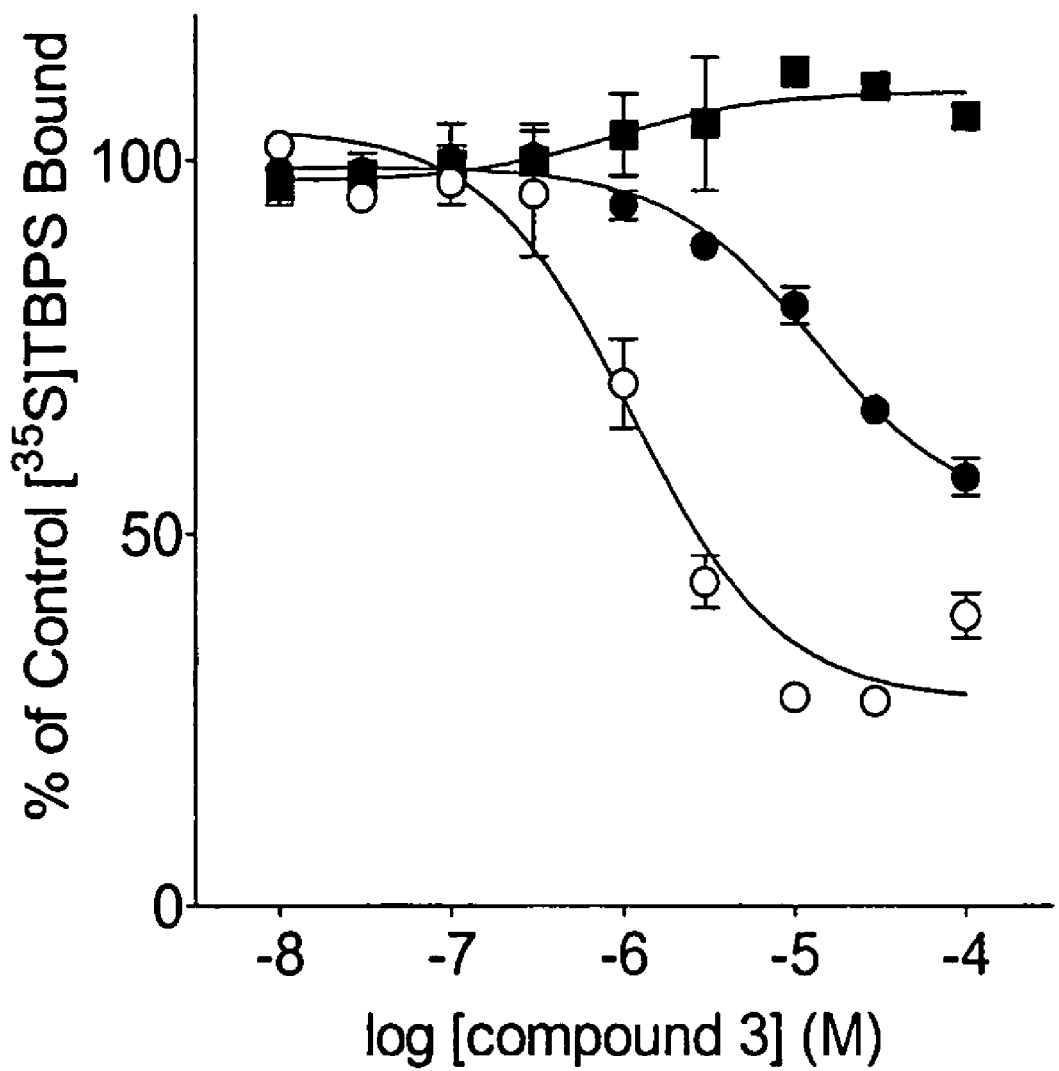
FIG. 5 depicts an effect of 7-chloro-1-ethyl-6-(1,2,3,4-tetrahydronaphthyl-1-amino)-4-oxo-1,4-dihydroquinoline-3-carboxylic acid (compound 3) on 2 nM [$^{35}$S]TBPS binding to rat cortex in the absence (open circles) or presence or of 3 μM (closed circle) and 10 μM (closed square) of the GABA$_A$ receptor antagonist (+)-bicuculline. These data demonstrate the absolute dependence of compound 3 on GABA for efficacy and that compound 3 is allosterically coupled to and does not act directly on the [$^{35}$S]TBPS site.
Figure 6:
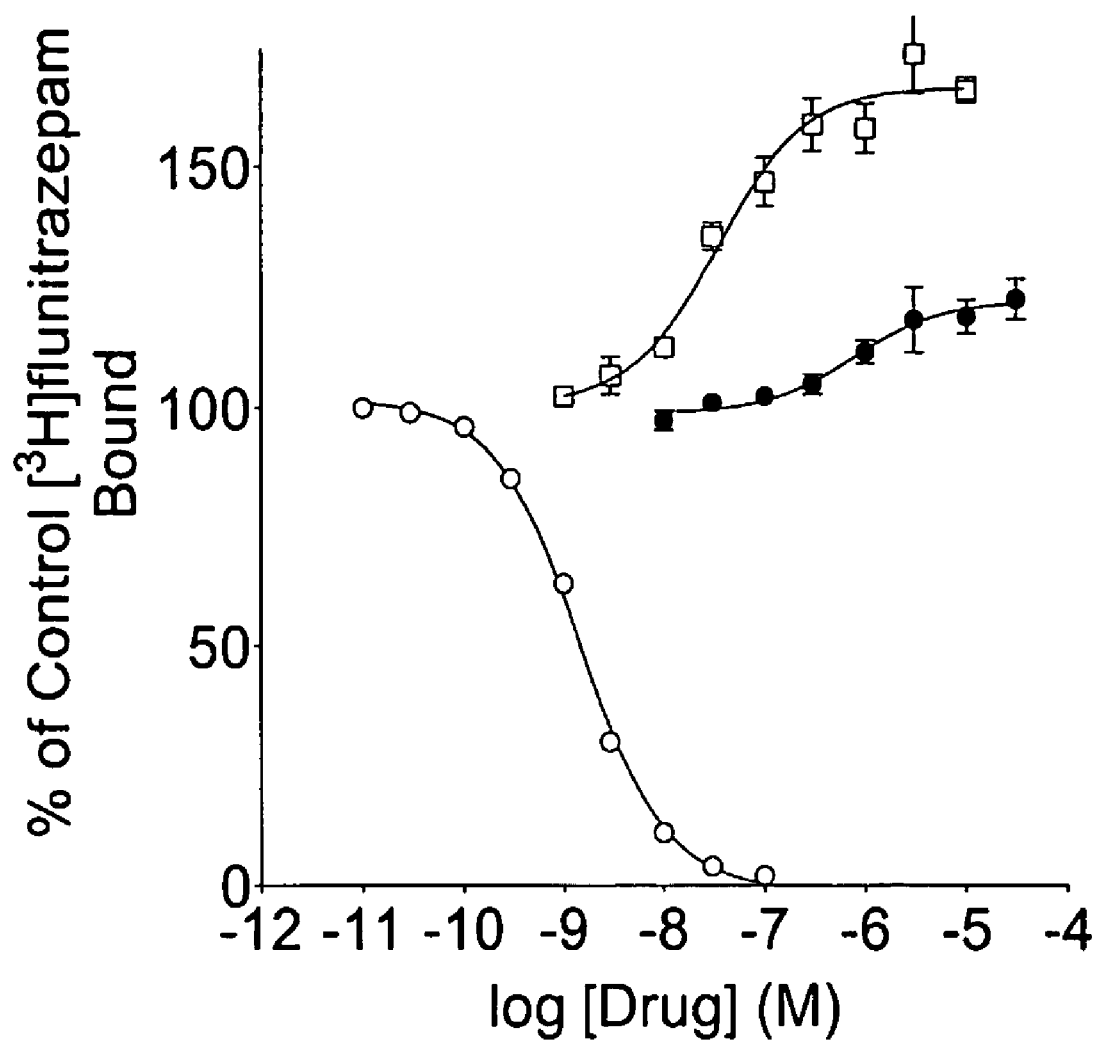
FIG. 6 depicts an effect of 7-chloro-1-ethyl-6-(1,2,3,4-tetrahydronaphthyl-1-amino)-4-oxo-1,4-dihydroquinoline-3-carboxylic acid (compound 3, closed circle), clonazepam (open circle) and 5α-pregnan-3α-ol-20-one (3α,5α-P, open square) on 0.2 nM [$^3$H]flunitrazepam binding to BZ receptors in rat cortex. These data demonstrate that compound 3 is allosterically coupled to and does not act directly on the BZ receptor.
Figure 7:
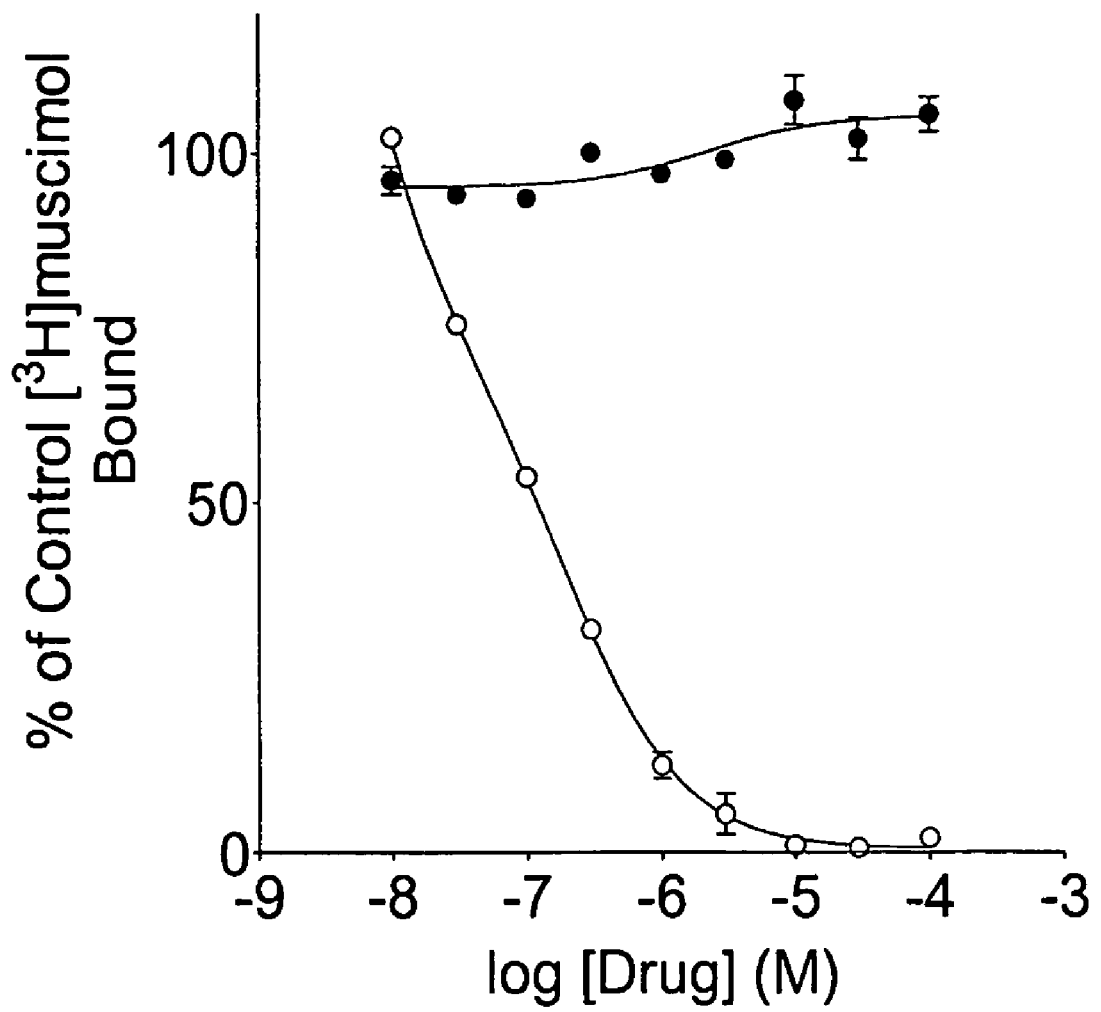
FIG. 7 depicts an effect of 7-chloro-1-ethyl-6-(1,2,3,4-tetrahydronaphthyl-1-amino)-4-oxo-1,4-dihydroquinoline-3-carboxylic acid (compound 3, closed circle) and GABA (open circle) on 5 nM [$^3$H]muscimol binding to the GABA$_A$ receptor in rat cortex. These data demonstrate that compound 3 does not act directly on the GABA$_A$ receptor.
Figure 8:
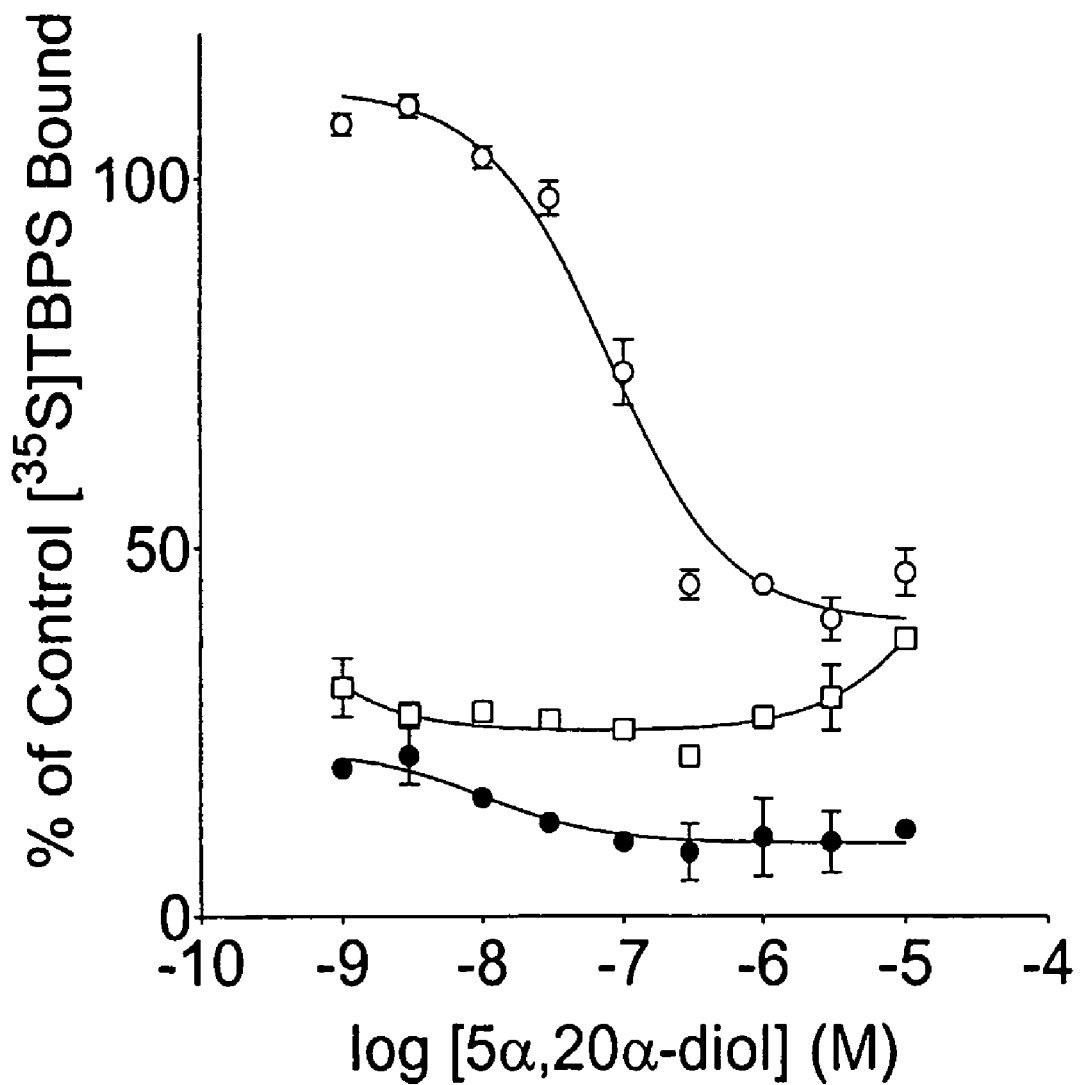
FIG. 8 depicts an effect of 10 μM 7-chloro-1-ethyl-6-(1,2,3,4-tetrahydronaphthyl-1-amino)-4-oxo-1,4-dihydro-quinoline-3-carboxylic acid (compound 3, closed circle) or 100 nM 3α,5α-P (open square) on 5α-pregnan-3α,20α-diol (5α,20α-diol, open circle) inhibition of 2 nM [$^{35}$S]TBPS binding to rat cortex. As predicted, increasing concentrations of 5α,20α-diol (a partial agonist) antagonize the effect of 3α,5α-P (a full agonist). The inability of 5α,20α-diol to antagonize the effect of compound 3 demonstrates that compound 3 does not act directly on the neurosteroid site of the GRC.
Figure 9:
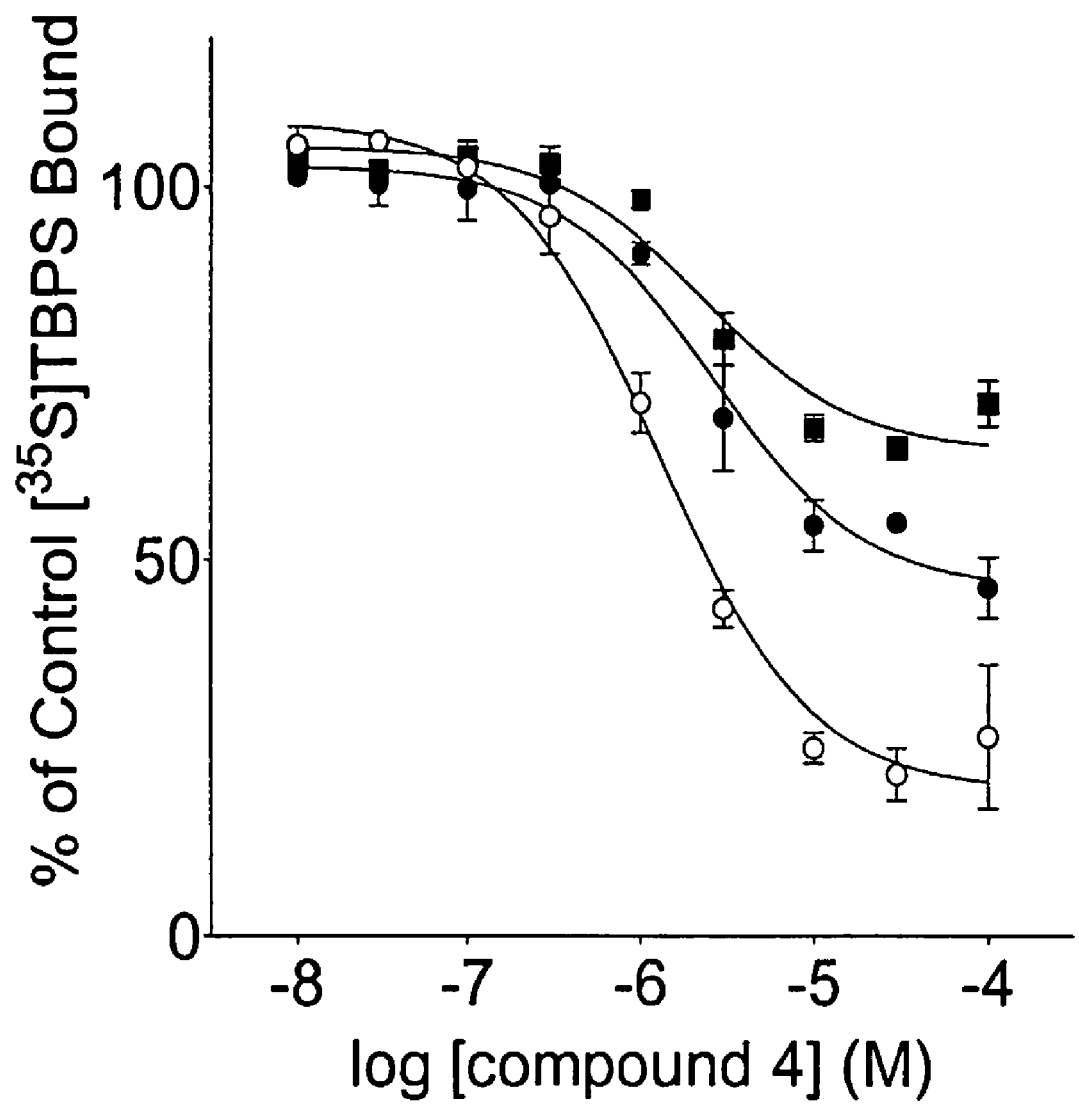
FIG. 9 depicts the effect of 7-chloro-1-ethyl-6-(1,2,3,4-tetrahydronaphthyl-1-amino)-4-oxo-1,4-dihydroquinoline-3-carboxylic acid (compound 3) on 2 nM [$^{35}$S]TBPS binding to rat cortex in the absence (open circle) or presence of 30 μM norfloxacin (closed circle) and 100 μM norfloxacin (closed square). The inability of norfloxacin to produce a dose-dependent rightward parallel shift of the compound 3 dose-response demonstrates that compound 3 does not act directly at the same site as the antibacterial quinolone norfloxacin.
Figure 10:
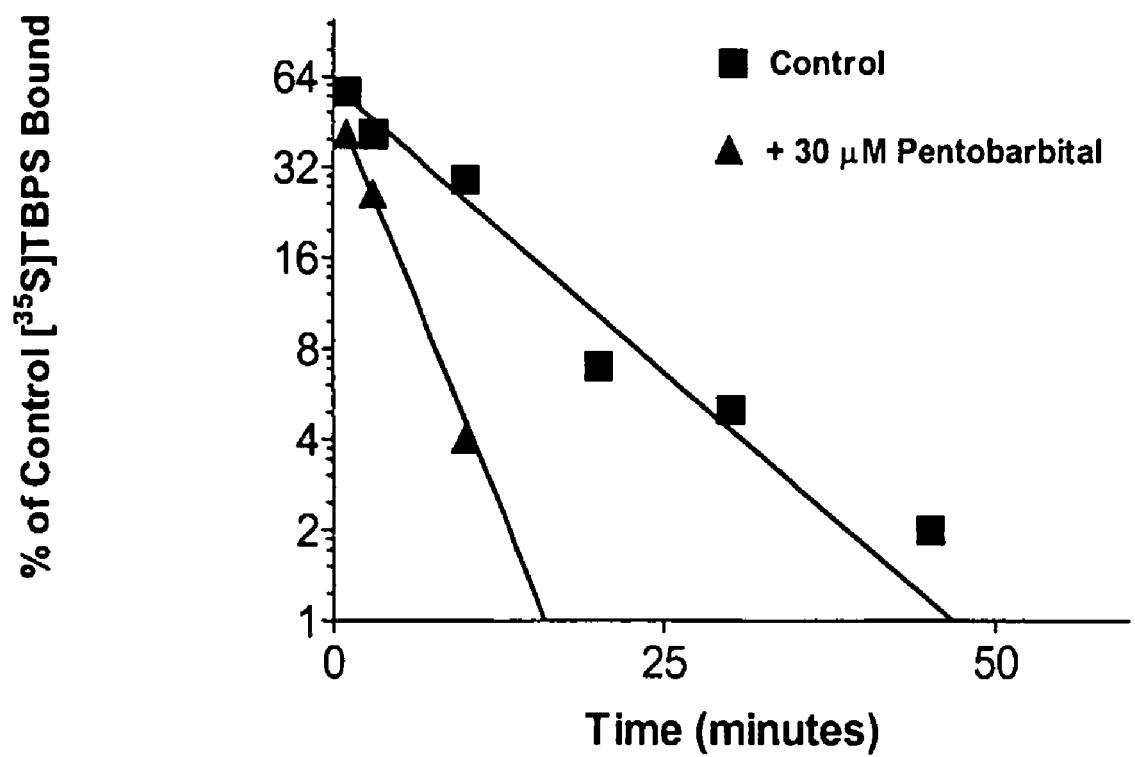
FIG. 10 depicts the dissociation of 2 nM [$^{35}$S]TBPS binding from rat cortex initiated by 10 μM 7-chloro-1-ethyl-6-(1,2,3,4-tetrahydronaphthyl-1-amino)-4-oxo-1,4-dihydroquinoline-3-carboxylic acid (compound 3) in the absence (closed square) or presence (closed triangle) of 30 μM pentobarbital. The ability of pentobarbital to accelerate the dissociation of [$^{35}$S]TBPS binding indicates that compound 3 and the barbiturate pentobarbital do not share a common site of action.
Figure 11:
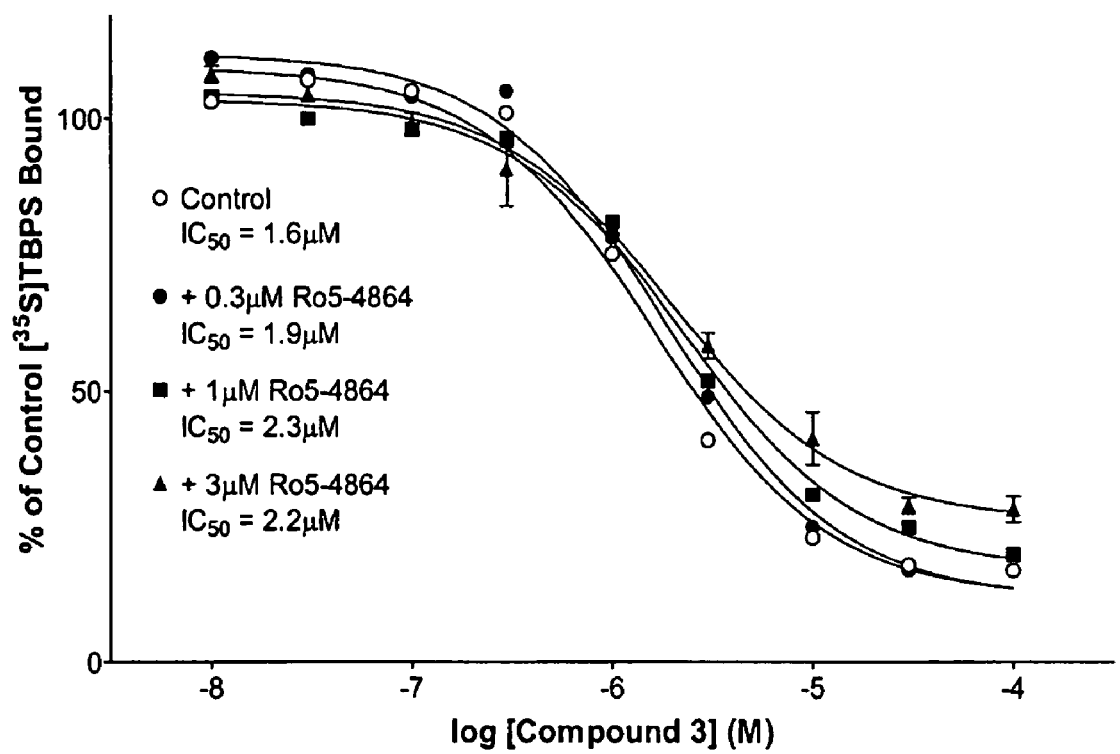
FIG. 11 depicts the effect of 7-chloro-1-ethyl-6-(1,2,3,4-tetrahydronaphthyl-1-amino)-4-oxo-1,4-dihydroquinoline-3-carboxylic acid (compound 3) on 2 nM [$^{35}$S]TBPS binding to rat cortex in the absence (open circle) or presence of 0.3 μM (closed circle), 1 μM (closed square) and 30 μM Ro5-4864 (4'-chlorodiazepam, closed triangle). The inability of 4'-chlorodiazepam to produce a dose-dependent rightward parallel shift of the compound 3/[$^{35}$S] TBPS dose-response curve demonstrates that compound 3 does not act directly at the same site as 4'-chlorodiazepam.
Figure 12:
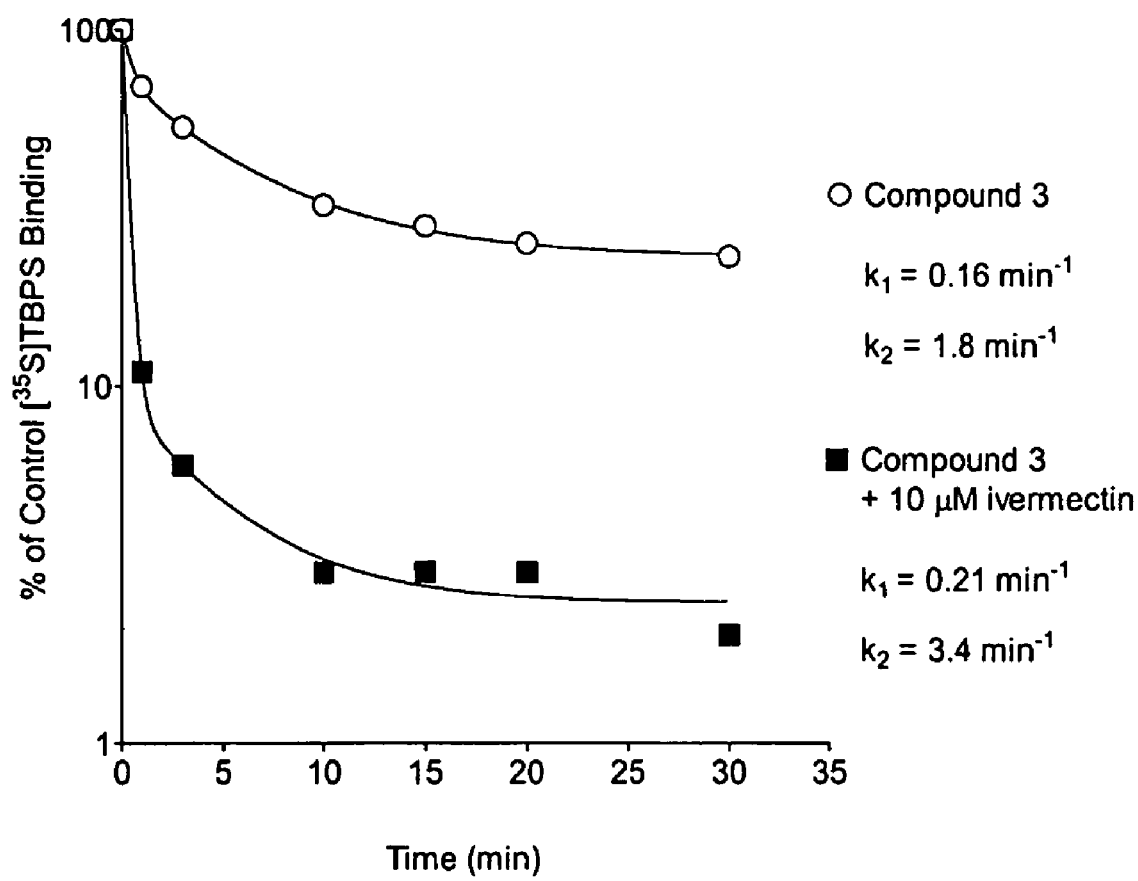
FIG. 12 depicts the dissociation of 2 nM [$^{35}$S]TBPS binding from mouse forebrain initiated by 10 μM 7-chloro-1-ethyl-6-(1,2,3,4-tetrahydronaphthyl-1-amino)-4-oxo-1,4-dihydroquinoline-3-carboxylic acid (compound 3) in the absence (open circle) or presence (closed square) of 10 μM ivermectin. The ability of ivermectin to accelerate the dissociation of [$^{35}$S]TBPS binding indicates that compound 3 and ivermectin do not share a common site of action.
Figure 13:
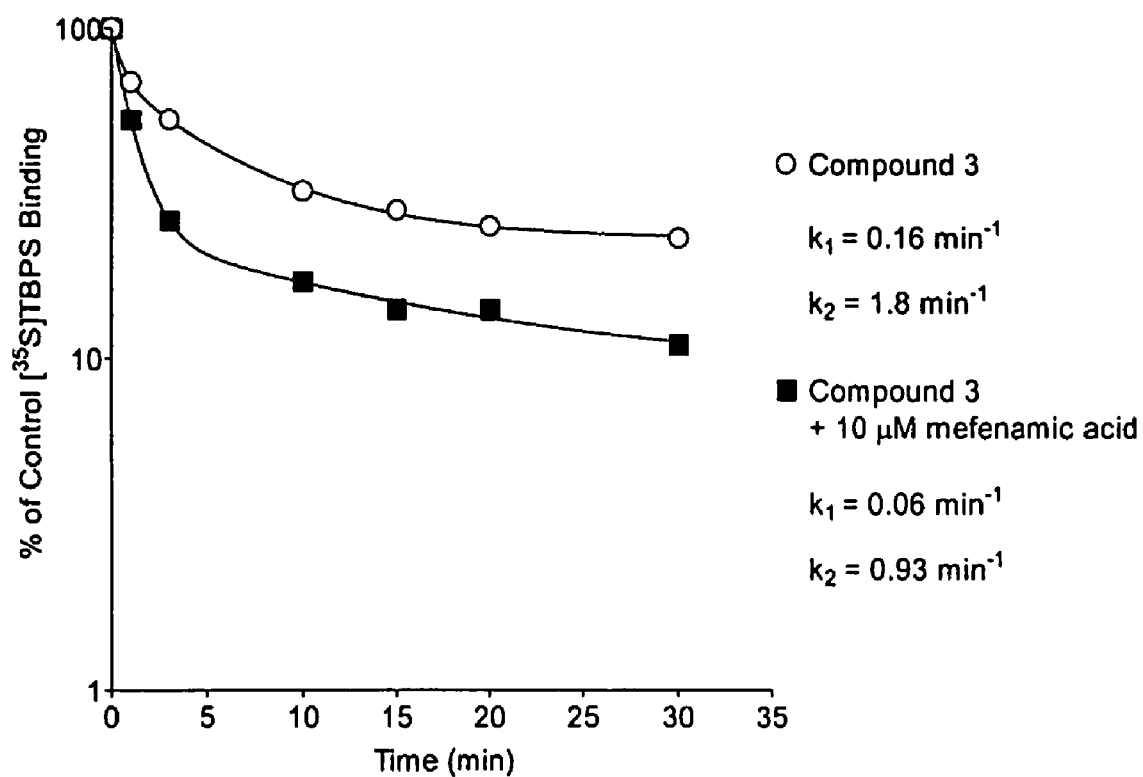
FIG. 13 depicts the dissociation of 2 nM [$^{35}$S]TBPS binding from mouse forebrain initiated by 10 μM 7-chloro-1-ethyl-6-(1,2,3,4-tetrahydronaphthyl-1-amino)-4-oxo-1,4-dihydroquinoline-3-carboxylic acid (compound 3) in the absence (open circle) or presence (closed square) of 10 μM mefenamic acid. The ability of mefenamic acid to accelerate the dissociation of [$^{35}$S]TBPS binding indicates that compound 3 and mefenamic acid do not share a common site of action.
Figure 14:
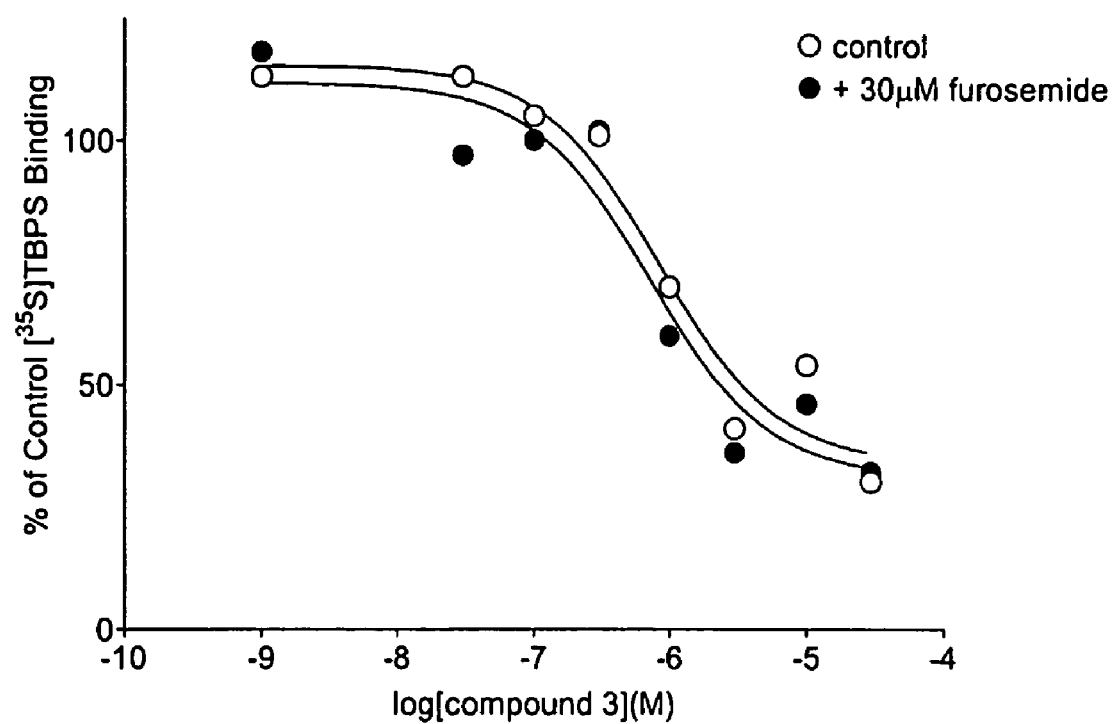
FIG. 14 depicts the effect of 7-chloro-1-ethyl-6-(1,2,3,4-tetrahydronaphthyl-1-amino)-4-oxo-1,4-dihydroquinoline-3-carboxylic acid (compound 3) on 2 nM [$^{35}$S]TBPS binding to rat cerebellum in the absence (open circle) or presence of 30 μM furosemide (closed circle). The inability of furosemide to produce a dose-dependent rightward parallel shift of the compound 3 dose-response demonstrates that compound 3 does not act directly at the same site on the GRC as the loop-diuretic furosemide.

The compounds useful in this aspect of the invention are substituted quinolones represented by Formula I:

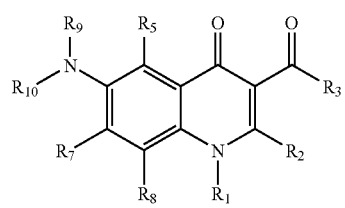

I or a pharmaceutically acceptable salt, prodrug or solvate thereof, wherein:

$R_1$ is selected from the group consisting of hydrogen; an optionally substituted alkyl, amino, aryl and aralkyl;

each $R_2$ is selected from the group consisting of hydrogen and optionally substituted alkyl;

each $R_3$ is selected from the group consisting of hydrogen, optionally substituted alkyl; a group $OR_{11}$ and $NR_{12}R_{13}$;

$R_5$, $R_7$ and $R_8$ are independently selected from the group consisting of hydrogen, an optionally substituted alkyl, and halogen;

$R_9$ and $R_{10}$ are independently selected from the group consisting of hydrogen, optionally substituted alkyl, aralkyl, cycloalkyl and cycloaralkyl; or $R_9$ and $R_{10}$ are taken together with the nitrogen atom to which they are attached to form a heterocyclic ring with the proviso that $R_9$ and $R_{10}$ are not both hydrogen at the same time;

$R_{11}$ is selected from the group consisting of hydrogen, an alkali metal, a negative charge and optionally substituted alkyl;

$R_{12}$ and $R_{13}$ are independently selected from the group consisting of hydrogen, optionally substituted alkyl, aralkyl, aryl, cycloalkyl and cycloaralkyl; or $R_{12}$ and $R_{13}$ are taken together with the nitrogen atom to which they are attached to form a heterocyclic ring.

The invention also relates to quinolones represented by Formula II:

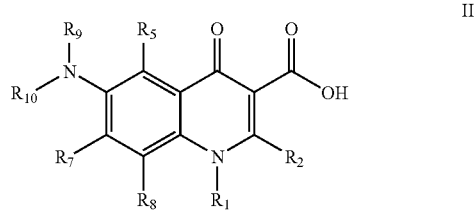

II or a pharmaceutically acceptable salt, prodrug or solvate thereof, wherein:

$R_1$ is selected from the group consisting of hydrogen; an optionally substituted alkyl, and aralkyl;

each $R_2$ is selected from the group consisting of hydrogen and optionally substituted alkyl;

$R_5$, $R_7$ and $R_8$ are independently selected from the group consisting of hydrogen, an optionally substituted alkyl, and halogen;

$R_9$ and $R_{10}$ are independently selected from the group consisting of optionally substituted alkyl, aralkyl, cycloalkyl and cycloaralkyl; or $R_9$ and $R_{10}$ are taken together with the nitrogen atom to which they are attached to form a heterocyclic ring.

Also, the invention relates to compounds of Formula III:

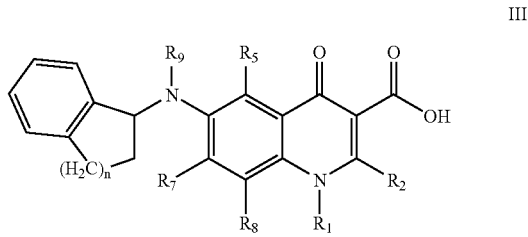

III or a pharmaceutically acceptable salt, prodrug or solvate thereof, wherein:

$R_1$, $R_2$, $R_5$, $R_7$, $R_8$, $R_9$ are defined previously with respect to Formulae I and II and n is an integer 0, 1, 2, 3 or 4.

For use in medicine, the salts of the compounds of Formula I-III will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, methanesulfonic acid, fumaric acid, maleic acid, succinic acid, acetic acid, benzoic acid, oxalic acid, citric acid, tartaric acid, or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of Formula I above. In general, such prodrugs will be functional derivatives of the compounds of Formula I which are readily convertible in vivo into the required compound of Formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention.

Useful halogen groups include fluorine, chlorine, bromine and iodine.

Useful alkyl groups include straight chain and branched C1-20 alkyl groups, more preferably, C5-20 alkyl groups. Typical C5-20 alkyl groups include n-penyl, n-hexyl, n-heptyl, n-octyl, n-nonyl, n-decyl, n-undecyl, n-dodecyl, n-tricedyl, n-tetradecyl, n-pentadecyl, n-hexadecyl, n-heptadecyl, n-octadecyl, n-nonadecyl and eicosanyl groups.

Useful aryl groups are $C_{6-14}$ aryl, especially $C_{6-10}$ aryl. Typical $C_{6-14}$ aryl groups include phenyl, naphthyl, anthracyl, indenyl, and biphenyl groups.

Useful arylalkyl groups include any of the above-mentioned C1-20 alkyl groups substituted with any of the above-mentioned C6-10 aryl groups. Useful arylalkyl groups include benzyl and phenethyl.

Useful cycloalkylalkyl groups include any of the above-mentioned C1-20 alkyl groups substituted with any of the previously mentioned cycloalkyl groups. Examples of useful cycloalkylalkyl groups include cyclohexylmethyl and cyclopropylmethyl groups.

Useful halomethyl groups include C1-20 alkyl groups substituted with one or more fluorine, chlorine, bromine or iodine atoms, including fluoromethyl, difluoromethyl, trifluoromethyl and 1,1-difluoroethyl groups.

Useful hydroxyalkyl groups include C1-20 alkyl groups substituted by hydroxy, including hydroxymethyl, 1- and 2-hydroxyethyl and 1-hydroxypropyl groups.

Useful alkoxy groups include oxygen substitution by one of the C1-20 alkyl groups described above.

Useful alkylthio groups include sulfur substitution by one of the C1-20 alkyl groups described above including decyl- and hexadecylthio groups.

Useful alkylamino and dialkylamino are —$NHR_9$ and —$NR_9R_{10}$, wherein $R_9$ and $R_{10}$ are C1-20 alkyl groups.

Useful dialkylaminoalkyl groups include any of the above-mentioned C1-20 alkyl groups substituted by any of the previously mentioned dialkylamino groups.

Useful alkylthiol groups include any of the above-mentioned C1-20 alkyl groups substituted by a —SH group.

A carboxy group is —COOH.

An amino group is —$NH_2$.

The term heterocyclic is used herein to mean saturated or wholly or partially unsaturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or nitrogen if the resulting compound is stable. Examples include, but are not limited to pyrrolidine, piperidine, piperazine, morpholine, 1,2,3,4-tetrahydroquinoline, and the like.

Optional substituents on $R_1$ to $R_{13}$ include any one of halo, halo($C_{1-20}$)alkyl, aryl, cycloalkyl, $C_{1-20}$alkyl, aryl($C_{1-20}$)alkyl, cycloalkyl($C_{1-20}$)alkyl, hydroxy($C_{1-20}$)alkyl, amino($C_{1-20}$)alkyl, alkoxy($C_{1-20}$)alkyl, amino, hydroxy, thiol, alkoxy, and $C_{1-20}$alkylthio groups mentioned above. Preferred optional substituents include: halo, halo($C_{1-6}$)alkyl, amino($C_{1-6}$)alkyl, alkoxy and amino.

The synthesis of compounds of Formula I where $R_7$=Cl and $R_{10}$=H can be accomplished by reacting a primary amine, $R_9NH_2$, in 1-methyl-2-pyrrolidinone (NMP) with 7-chloro-1-ethyl-6-fluoro-4-oxo-1,4-dihydroquinoline-3-carboxylic acid (2, commercially available from Acros, see Scheme 1).

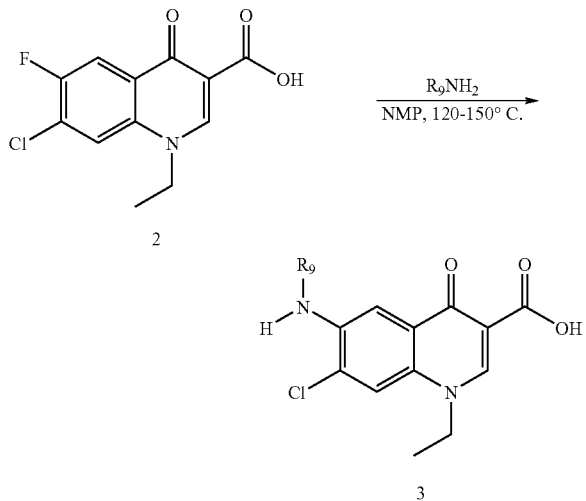

Examples of $R_gNH_2$ include substituted benzylamines, substituted phenethylamines, 3-phenylaminopropane, 1-aminoindan and 1-amino-1,2,3,4-tetrahydronaphthlene.

For the synthesis of compounds of Formula I with groups other than ethyl and cyclopropyl at $R_1$, the 6-fluoro-7-chloro starting material (8) can be prepared as in Scheme 2 starting from commercially available 2,4-dichloro-5-fluorobenzoyl chloride (4, Lancaster Synthesis).

Scheme 2

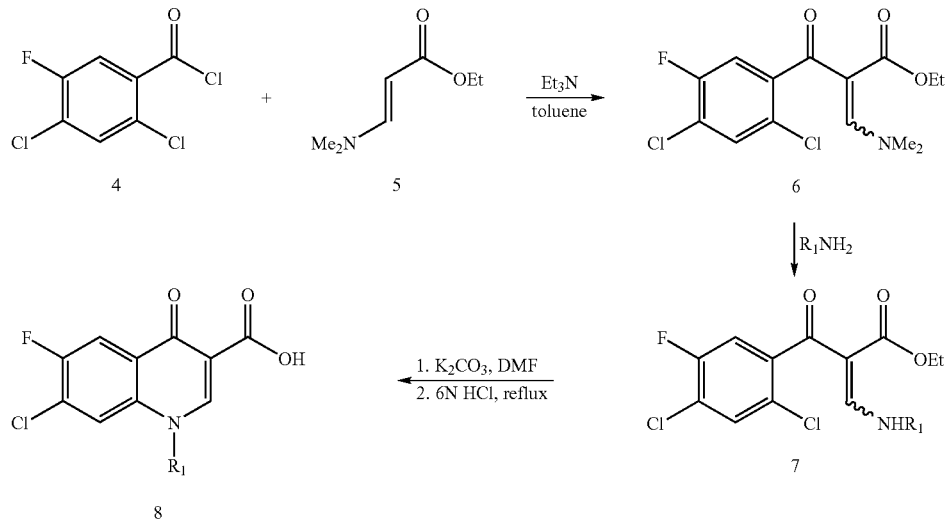

Examples of $R_1NH_2$ include 2-fluoroethylamine, optionally substituted benzylamines and optionally substituted phenethylamines. Other methods for assembling the quinolone ring can be used as described in Atkins, et al, Org. Process Res. & Develop. (1997),1, 185-197.

In Vitro Binding Assay 1

[$^{35}$S]TBPS binding assay. The cortex from male Sprague-Dawley rats (weighing 160-200 g) was removed immediately after decapitation and dissected over ice. A $P_2$ homogenate was prepared for binding assay as previously described (Gee K W Phenylquinolines PK 8165 and PK 9084 allosterically modulate [$^{35}$S]t-butylbicyclophosphorothionate binding to a chloride ionophore in rat brain via a novel Ro5 4864 site. *J. Pharmacol. Exp. Ther.* 240:747-753, 1987). The tissue was homogenized in 0.32M sucrose (J. T. Baker Chemical Co., Phillipsburg, N.J., USA) with a Teflon-coated pestle, followed by centrifugation at 1,000× g for 10 min. The supernatant was collected and centrifuged at 9,000× g for 20 min. The resultant $P_2$ pellet was resuspended in ice-cold 50 mM sodium potassium phosphate (J. T. Baker) buffer (pH 7.4) containing 200 mM NaCl (J. T. Baker) and used immediately in binding assays. A 2 nM concentration of [$^{35}$S]TBPS (86 Ci/mmol; New England Nuclear, Boston, Mass., USA) was incubated with 100 μl of tissue homogenate (10% w/v) in the presence or absence of 5 μM GABA (Sigma Chem. Co., St. Louis, Mo.) and 5 μl aliquots of test drug dissolved in dimethyl sulfoxide (Sigma Chem. Co.) (≦10 μl of solvent used in all assays). At the concentration (≦1%) used, dimethyl sulfoxide had no effect on specific [$^{35}$S]TBPS binding. All assays were brought to a final volume of 1 ml with 50 mM sodium potassium phosphate buffer (pH 7.4) containing 200 mM NaCl. Non-specific binding was defined as binding in the presence of 2 μM TBPS (NEN, Boston, Mass.) and accounted for ~30% of the total binding. Assays were terminated after a 90-min steady-state incubation at 25° C. by rapid filtration through glass fiber filters (no. 32; Schleicher & Schuell, Keene, N.H.). The dissociation kinetics of [$^{35}$S]TBPS binding were measured by initiating dissociation by the addition of a saturating concentration of a known inhibitor of [$^{35}$S]TBPS binding or a test compound to tissue homogenates pre-equilibrated with 2 nM [$^{35}$S]TBPS followed by filtration at various time points after the addition of the known inhibitor or test compound. Allosteric modulators of the known inhibitor or test compound will modify the rate of dissociation under these conditions whereas agents acting at common site will not affect the rate. Filter-bound radioactivity was quantified by liquid scintillation spectrophotometry. The data were evaluated by nonlinear regression (GraphPad, Inc., San Diego, Calif.) to obtain $IC_{50}$ (concentration at which half-maximal inhibition of radioligand occurs) values.

In Vitro Binding Assay 2

[$^3$H]Flunitrazepam binding: assays were carried out under identical conditions, using an identical tissue preparation, as those used in the [$^{35}$S]TBPS binding assays with the exception that 1 μM GABA was added to all samples instead of 5 μM GABA. [$^3$H]Flunitrazepam, 0.2 nM (75 Ci/mmol, New England Nuclear, Boston, Mass.) was used to label BZ sites. Non-specific binding is defined as binding in the presence of 1 μM clonazepam. The data were evaluated by nonlinear regression to obtain $IC_{50}$ and $EC_{50}$ values.

In Vitro Binding Assay 3

[$^3$H]Muscimol binding assay: The cortex from male Sprague-Dawley rats (160-200 g) was removed immediately after euthanizing and dissected over ice. The tissue was homogenized in 15 vol of 0.32M sucrose followed by centrifugation for 10 min at 1000× g. The supernatant was transferred to a 38 mL polycarbonate tube (Beckman Instruments, Palo Alto Calif.) and centrifuged at 20,000× g for 20 min. The membrane pellet was resuspended in 10 vol of $dH_2O$ and centrifuged at 8,000× g for 20 min. The resulting pellet was washed with $dH_2O$ once and with $Na^+$-free assay buffer (40 mM $KH_2PO_4$, 100 mM KCl, pH 7.4). The pellet was resuspended in 35 mL of $Na^+$-free assay buffer, incubated at 37° C. for thirty minutes and then centrifuged 31,000× g for twenty minutes. The final pellet was resuspended in 10 vol of $Na^+$-free assay buffer. Protein concentration of membrane preparations was ~1 mg/mL by BCA reagent protein assay. Aliquots of membrane suspension (100 μL) were incubated in $Na^+$-free assay buffer with 5 nM [$^3$H]muscimol (25 Ci/mmol, New England Nuclear, Boston, Mass.) and 5 µL of dimethylsulfoxide (DMSO) or drug dissolved in DMSO. The final volume of the incubation medium was 1 mL. Non-specific binding was defined as binding in the presence of 1 mM GABA. After addition of membranes, tubes were briefly vortexed and incubated at 4° C. in the dark. The incubation was terminated after 60 min by rapid filtration through glass fiber filters followed by three washes with ice-cold assay buffer. Filter-bound radioactivity was quantified by LSC after an overnight extraction. The data were evaluated by nonlinear regression to obtain $IC_{50}$ and $EC_{50}$ values.

Electrophysiological Assay 1.

Pregnant Sprague-Dawley rats, incubating embryos of 17-19 days gestation, were killed by cervical dislocation. The embryos were removed under aseptic conditions and the brains quickly excised and placed in Hank's balanced salt solution (HBSS, Gibco) at ambient room temperature (18-22° C.). The hippocampi were dissected out and chopped into fragments (~2 mm$^3$) and transferred into an enzyme solution containing (in mM): NaCl 116, KCl 5.4, NaHCO$_3$ 26, NaH$_2$PO$_4$ 1, CaCl$_2$ 1.5, MgSO$_4$ 1, EDTA 0.5, glucose 25, cysteine 1, and papain 20 U/ml (Sigma) and incubated at 37° C., 5% CO$_2$, 100% relative humidity for 1 hr. Tissue fragments were washed in HBSS containing 1 mg/ml of bovine serum albumin (BSA) and 1 mg/ml of ovomucoid (both Sigma). Tissue was transferred into a further 3-4 ml of this solution and gently triturated into a single cell suspension using a fire-polished Pasteur pipette. The single cell suspension was layered on to 5 ml HBSS containing 10 mg/ml of BSA and 10 mg/ml of ovomucoid and centrifuged at 100× g for 10 min. The supernatent was discarded and the cells resuspended in 3-4 ml of glutamine-free minimal essential media (MEM, Gibco) supplemented with heat-inactivated fetal calf serum (5% v/v Gibco), heat-inactivated horse serum (5% v/v Gibco), streptomycin and penicillin (50 µg/ml and 5000 i.u./ml, respectively), glutamine and glucose (final concentrations 2 mM and 20 mM [Gibco and BDH] respectively). Approximately $1-2 \times 10^5$ cells were plated out on to each 35 mm (Falcon "Primaria") tissue culture dish which contained ~1 ml of the sera-enriched MEM. The plates were maintained at 37° C., in 5% CO$_2$, and 100% relative humidity until used in electrophysiological studies. Background proliferation of non-neuronal elements was suppressed with cytosine arabinoside (10 µM, Sigma) for 48 hr 7 days after initial dissociation.

Agonist evoked membrane currents were recorded from hippocampal neurons using the whole cell configuration of the patch-clamp technique. Neurons were voltaged clamped at −60 mV using a List electronics L/M EPC-7 converter head stage and amplifier. Cells were perfused with an external (bath) recording solution containing (in mM): NaCl 140, KCl 2.8, MgCl$_2$ 2, CaCl$_2$ 1 and HEPES-NaOH 10 (pH 7.2). Tetrodotoxin (TTX, 0.3 µM) was included in the recording solution to suppress synaptic activity. The external solution was delivered (at ~2 ml/min) by a Watson-Marlow flow pump via non-sterile tubing, which was connected to a plastic cannula (tip dia 1 mm). The input cannula was mounted on a Prior® micromanipulator and was positioned in close (<1 mm) proximity to the cell under study. Bath solution was withdrawn from the dish via a 19G needle connected by flexible tubing to an aquarium suction pump. The recording electrode was filled with an internal solution composed of (in mM): CsCl or KCl 140, MgCl$_2$ 2, CaCl$_2$ 0.1, EGTA 1.1 (free $Ca^{2+}$~$10^{-8}$ M), HEPES-NaOH 10, and ATP-Mg$^{2+}$ 2. The recording electrodes were fabricated from glass hematocrit tubes (Kimble sodalime tubes 73811) on a Narishige PB7 two stage electrode puller. Electrodes were coated within 100 µm of the tip with "Sylgard" (Dow Corning) and fire polished just before use. Agonists were applied locally to the soma of a voltage-clamped neuron by pressure ejection (1.4 Kpa, 10-80 msec, 0.1-0.033 Hz) from the tip of a modified recording pipette using a Picospritzer II device (General Valve Corporation). The agonist-containing pipette was positioned within 0.1 mm of the cell using a Leitz micromanipulator. The microscope and micromanipulators were all mounted on a vibration-free isolation air table (Wentworth) placed inside a Faraday cage. Agonist-evoked whole cell currents were monitored on a storage oscilloscope (Tektronix 2212), recorded, after digital pulse code modulation (frequency response 14 kHz, Sony PCM 701), and displayed on Multitrace (Electromed) pen chart recorder (frequency response 0.5 kHz). All drugs, other than the agonists, were applied to cells via the superfusion system. Agonist-evoked whole cell currents were measured at their peak. Responses in the presence of drugs expressed as the arithmetic mean ±SEM of responses in the absence (control) or drugs.

Electrophysiology Assay 2

GABA$_A$ subunit transfected HEK cells are maintained at 37° C. and 5% CO$_2$ using Dulbecco's Modified Eagle's Medium with L-glutamine and no sodium pyruvate (Irvine Scientific #9031, Irvine Calif.) and supplemented with 10% fetal bovine serum (Irvine Scientific #3000), 10 U/ml hygromycin B (Calbiochem #400051), and an antibiotic cocktail consisting of 100 µg/ml streptomycin sulfate, 0.25 µg/ml amphotericin B, 100 units/ml penicillin G (Gibco 15240-096, Gaithersburg Md.). Cells are passed by 2× wash with phosphate buffered saline (PBS) pH 7.4 and lifted using 1× trypsin/EDTA solution in PBS (0.5 mg/ml trypsin, 0.2 mg/ml EDTA, Irvine Scientific #9342) when confluency reaches ~90%.

GABA$_A$ subunit transfected HEK cells are grown to ~70% confluency on slide. Cells are transferred to a bath that is continuously perfused with extracellular saline. The extracellular medium contained 145 mM NaCl, 3 mM KCl, 1.5 mM CaCl$_2$, 1 mM MgCl$_2$, 5.5 mM d-glucose, and 10 mM HEPES, pH 7.4 at an osmolarity of 320-330 mosM. Recordings are performed at room temperature using the whole cell patch clamp technique. The patch pipette solution contained 147 mM N-methyl-D-glucamine hydrochloride, 5 mM CsCl, 5 mM K$_2$ATP, 5 mM HEPES, 1 mM MgCl$_2$, 0.1 mM CaCl$_2$, and 1.1 mM EGTA, pH 7.2, at an osmolarity of 315 mosM. Pipette-to-bath resistance is typically 3-5 Mohms. Cells are voltage clamped at −60 mV, and the chloride equilibrium potential was approximately 0 mV. Drugs are dissolved in extracellular medium and rapidly applied to the cell by local perfusion. A motor driven multi-channel switching system exchanged solutions in approximately 20 ms.

In vivo Pharmacology

Vogel Conflict

Adult male rats are randomly divided into groups of 6 rats/group. Animals were deprived of water overnight (24 hr). Food was freely available at time of thirsting. Thirty minutes after injection (i.p.) of test drug, positive control drug (diazepam, 1 mg/kg), or vehicle control rats are placed in a square Plexiglas box containing a stainless steel bottom connected to one side of a drinkometer circuit. At the other side of the drinkometer circuit a water bottle, placed so the drink tube extends into the Plexiglas box, is connected. When a subject drinks from the bottle the circuit is closed and an electric shock is delivered at the tube after seven licks are recorded. The number of licks in a 3 min session is recorded. Anti-anxiety agents will increase the number of shocks the animal is willing to endure to acquire water.

Light-Dark Transition

Male NSA mice (25-30 g) are used. The apparatus consists of an open-topped box divided into small and large area by a partition that has a hole at floor level. The small compartment is painted black and the large compartment white. The white compartment was illuminated with light and the black compartment with red light. The time spent in the light versus dark compartments and the number of transitions between compartments is recorded during a 5 min test session. Vehicle or test compounds are administered 30 min prior to the test. Diazepam is administered (i.p.) at 2 mg/kg as the positive control. Anti-anxiety agents will reduce the time the animals will spend in the dark compartment and increase the number of transitions between the two compartments.

Carriers

In addition to administering the compound as a raw chemical, the compounds of the invention may be administered as part of a pharmaceutical preparation containing suitable pharmaceutically acceptable carriers comprising excipients and auxiliaries, which facilitate processing of the compounds into preparations, which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings that, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropyrnethylcellulose phthalate, are used. Dye stuffs or pigments may be added to the tablets or dragee coatings, for example, for identification or in order to characterize combinations of active compound doses.

Other pharmaceutical preparations, which can be used orally, include push-fit capsules made of gelatin, as well as soft, sealed capsules made of gelatin and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which can be used rectally, include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules, which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances, which increase the viscosity of the suspension, and include, for example, sodium carboxymethyl cellulose, sorbitol, and/or dextran. Optionally, the suspension may also contain stabilizers.

EXAMPLE 1

7-Chloro-1-ethyl-6-(1,2,3,4-tetralydronaphtlyl-1-amino)-4-oxo-1,4-dilydroquinoline-3-carboxylic acid To a suspension of 7-chloro-1-ethyl-6-fluoro-4-oxo-1,4-dihydroquinoline-3-carboxylic acid (Acros; 6.02 g, 22.3 mmol) in 30 mL of 1-methyl-2-pyrrolidinone was added neat 1,2,3,4-tetrahydro-1-aminonaphthalene (20 mL, 20.5 g, 140 mmol) drop-wise via syringe. The resulting light yellow mixture was placed in an oil bath at 140° C. for 17 h. Once at rt, the reaction was added to 120 mL of an aq. 2N HCl solution and ice. The solid that formed was isolated by filtration, washed with an aq. 2N HCl solution (120 mL), water (2×100 mL), MeOH (3×50 mL) and EtOAc (50 mL). The solid that remained was then recrystallized from MeOH (1400 mL). The yellow needles that formed were isolated and washed with methanol (2×50 mL). This solid was then subjected to flash column chromatography. A solution of the solid in 35 mL of 4% MeOH/$CH_2Cl_2$ was added to 16 cm of silica in a 5 cm dia. column. Elution with 1 L of 7.5% and 500 mL of 10% MeOH/$CH_2Cl_2$ gave 968 mg (11%) of the title compound as a yellow solid, mp 246-247° C. $^1$H NMR (400 MHz, DMSO-$d_6$) δ 15.14 (s, 1 H), 8.66 (s, 1 H), 7.80 (s, 1 H), 7.63 (s, 1H), 7.32 (d, 1 H, J=7.7 Hz), 7.26-7.16 (m, 3H), 4.90 (s, 2H), 4.33 (q, 2 H, J=7.2 Hz), 2.92-2.80 (m, 2 H), 2.12-2.00 (m, 2 H), 1.92-1.86 (m, 2 H), 1.60 (t, 3 H, J=7.2 Hz). MS (M+Na)$^+$ 0419. Anal Calcd. for $C_{22}H_{21}ClN_2O_3$+0.25 HCl: C, 65.08; H, 5.28; Cl, 10.92; N, 6.90. Found: C, 65.09; H, 5.33; Cl, 10.85; N, 6.81.

The following compounds were prepared by using the method described above:

(R)-7-Chloro-1-ethyl-6-(1,2,3,4-tetrahydronaphthyl-1-amino)-4-oxo-1,4-dihydroquinoline-3-carboxylic acid;

(S)-7-Chloro-1-ethyl-6-(1,2,3,4-tetrahydronaphthyl-1-amino)-4-oxo-1,4-dihydroquinoline-3-carboxylic acid;

7-Chloro-1-ethyl-6-(6-methoxy-1,2,3,4-tetrahydronaphthyl-1-amino)-4-oxo-1,4-dihydroquinoline-3-carboxylic acid;

7-Chloro-1-ethyl-6-(1-aminoindanyl)-4-oxo-1,4-dihydroquinoline-3-carboxylic acid;

7-Chloro-1-ethyl-6-(5-methyl-1-aminoindanyl)-4-oxo-1,4-dihydroquinoline-3-carboxylic acid;

7-Chloro-1-ethyl-6-(2-aminoindanyl)-4-oxo-1,4-dihydroquinoline-3-carboxylic acid;

7-Chloro-1-ethyl-6-(benzylamino)-4-oxo-1,4-dihydroquinoline-3-carboxylic acid;

7-Chloro-1-ethyl-6-(2-phenethylamino)-4-oxo-1,4-dihydroquinoline-3-carboxylic acid. The reaction was performed as in Example I except that the crude reaction mixture was diluted with EtOAc giving the desired compound as a white solid. $^1$H NMR (400 MHz, DMSO-$d_6$) δ 15.15 (br s, 1H), 8.64 (s, 1H), 7.63 (s, 1H), 7.58 (s, 1H), 7.37-7.33 (m, 2H), 7.29-7.24 (m, 3H), 4.68 (t, 1H, J=5.4 Hz), 4.31 (q, 2H, J=7.3 Hz), 3.59 (q, 2H, J=6.4 Hz), 3.03 (t, 2H, J=6.9 Hz), 1.58 (t, 3H, J=7.3 Hz);

7-Chloro-1-methyl-6-(1,2,3,4-tetrahydronaphthyl-1-amino)-4-oxo-1,4-dihydroquinoline-3-carboxylic acid, $^1$H NMR (400 MHz, CDCl$_3$)δ 15.10 (s, 1H), 8.62 (s, 1H), 7.77 (s, 1H), 7.62 (s, 1H), 7.33 (d, 1H, J=7.0 Hz), 7.25-7.17 (m, 3H), 4.91 (br, s, 2H), 3.99 (s, 3H), 2.86 (m, 2H), 2.11-2.01 (m, 2 H), 1.91-1.87 (m, 2H);

7-Chloro-1-ethyl-6-[4-methoxy(phenethylamino)]-4-oxo-1,4-dihydroquinoline-3-carboxylic acid;

7-Chloro-1-cyclopropyl-6-[4-methoxy(phenethylamino)]-4-oxo-1,4-dihydroquinoline-3-carboxylic acid;

7-Chloro-1-ethyl-6-[3-methoxy(phenethylamino)]-4-oxo-1,4-dihydroquinoline-3-carboxylic acid;

7-Chloro-1-ethyl-6-[2-methoxy(phenethylamino)]-4-oxo-1,4-dihydroquinoline-3-carboxylic acid;

7-Chloro-1-ethyl-6-[4-bromo(phenethylamino)]-4-oxo-1,4-dihydroquinoline-3-carboxylic acid;

7-Chloro-1-ethyl-6-[4-chloro(phenethylamino)]-4-oxo-1,4-dihydroquinoline-3-carboxylic acid;

7-Chloro-1-ethyl-6-[4-fluoro(phenethylamino)]-4-oxo-1,4-dihydroquinoline-3-carboxylic acid;

7-Chloro-1-ethyl-6-(3-phenylpropylamino)-4-oxo-1,4-dihydroquinoline-3-carboxylic acid;

7-Chloro-1-ethyl-6-(4-phenylbutylamino)-4-oxo-1,4-dihydroquinoline-3-carboxylic acid;

7-Chloro-1-ethyl-6-(4-phenylbutyl-2-amino)-4-oxo-1,4-dihydroquinoline-3-carboxylic acid;

7-Chloro-1-ethyl-6-(2-phenylcyclopropylamino)-4-oxo-1,4-dihydroquinoline-3-carboxylic acid;

7-Chloro-1-ethyl-6-(2-phenylcyclopropylamino)-4-oxo-1,4-dihydroquinoline-3-carboxylic acid;

7-Chloro-1-ethyl-6-(1-naphthylethyl-1-amino)-4-oxo-1,4-dihydroquinoline-3-carboxylic acid;

7-Chloro-1-ethyl-6-(1-naphthylmethylamino)-4-oxo-1,4-dihydroquinoline-3-carboxylic acid and 7-Chloro-1-ethyl-6-(2-phenoxyethylamino)-4-oxo-1,4-dihydroquinoline-3-carboxylic acid.

EXAMPLE 2

7-Chloro-1-ethyl-6-(1,2,3,4-tetrahydronaphthyl-1-amino)-4-oxo-1,4-dihydroquinoline-3-(n-propyl) carboxamide To a solution of 7-chloro-1-ethyl-6-(1,2,3,4-tetrahydronaphthyl-1-amino)-4-oxo-1,4-dihydroquinoline-3-carboxylic acid (37 mg, 0.093 mmol) in 5 mL of CHCl$_3$ at −10° C. was added neat Et$_3$N (30 μL, 22 mg, 0.22 mmol) and benzyl chloroformate (17 μL, 20 mg, 0.117 mmol). After stirring cold for 45 m, neat propylamine (10 μL, 7.2 mg, 0.122 mmol) was added via syringe to the reaction at −20° C. The reaction was then allowed to warm to rt over 2 h and added to 7 mL each of a 10% aq. K$_2$CO$_3$ solution and CHCl$_3$. The organic layer was separated and washed with water (2×10 mL), dried (Na$_2$SO$_4$), filtered and concentrated to dryness. The residue was taken up in CH$_2$Cl$_2$ and added to 10 cm of flash silica gel in a 2 cm dia. column. Elution with 100% CH$_2$Cl$_2$ (100 mL) and 2.5% MeOH/CH$_2$Cl$_2$ (200 mL) gave 37 mg (91%) of the title compound as a yellow solid.

The following compounds were prepared by using the general method given in Example 2:

7-Chloro-1-ethyl-6-(1,2,3,4-tetrahydronaphthyl-1-amino)-4-oxo-1,4-dihydroquinoline-3-(2-phenethyl)carboxamide;

7-Chloro-1-ethyl-6-(1,2,3,4-tetrahydronaphthyl-1-amino)-4-oxo-1,4-dihydroquinoline-3-(2-dimethylaminoethyl)carboxamide and 7-Chloro-1-ethyl-6-(1,2,3,4-tetrahydronaphthyl-1-amino)-4-oxo-1,4-dihydroquinoline-3-(pyridylmethylamino)carboxamide.

EXAMPLE 3

7-Chloro-]-(2-phenethyl)-6-(1,2,3,4-tetrahydronaphthyl-1-amino)-4-oxo-1,4-dihydroquinoline-3-carboxylic acid a. Ethyl 2-(2,4-dichloro-5-fluorobenzoyl)-3-(dimethylamino)acrylate. A mixture of ethyl 3,3-dimethylaminoacrylate (3.10 g, 21.6 mmol) and N,N-diisopropylethylamine (8.0 mL, 5.94 g, 45.9 mmol) was stirred at rt and a solution of 2,4-dichloro-5-fluorobenzoyl chloride (4.92 g, 21.6 mmol) was added drop-wise via addition funnel over 20 m. The cloudy yellow solution that formed was placed in an oil bath at 85-90° C. After 3 h, the mixture that formed was filtered and the solid was washed with benzene. The dark filtrate was concentrated and the residue was triturated with hexanes (50 mL). The solid that didn't dissolve was collected and washed with hexanes (20 mL). The resulting solid was partitioned between water and EtOAc. The EtOAc layer was washed with water (3×25 mL), brine, dried (Na$_2$SO$_4$), filtered and concentrated to 5.0 g (69%) of the desired compound.

b. Ethyl 2-(2,4-dichloro-5-fluorobenzoyl)-3-(2-phenethylamino)acrylate. A suspension of ethyl 2-(2,4-dichloro-5-fluorobenzoyl)-3-(dimethylamino)acrylate (1.014 g, 3.03 mmol) in 10 mL of EtOH was treated with neat phenethylamine (0.4 mL, 386 mg, 3.19 mmol) added drop-wise via syringe. After stirring at rt for 75 m, the mixture that formed was filtered and the solid was washed with EtOH leaving 620 mg (50%) of the acrylate as a white solid.

c. Ethyl 7-chloro-6-fluoro-1-(2-phenethyl)-4-oxo-1,4-dihydroquinoline-3-carboxylate. To a solution of ethyl 2-(2, 4-dichloro-5-fluorobenzoyl)-3-(2-phenethylamino)acrylate (656 mg, 1.60 mmol) in 1.5 mL of DMF was added solid K$_2$CO$_3$ (227 mg, 1.64 mmol). The resulting mixture was placed in an oil bath at 130° C. for 16 h. Once at rt, the reaction was added to water. The gummy solid that formed was partitioned between water and EtOAc. The aq. layer was extracted with EtOAc (2×10 mL). The pooled organic layers were washed with water (2×15 mL), brine and dried (Na$_2$SO$_4$). The solvent was removed in vacuo, giving 572 mg (96%) of the desired quinolone.

d. 7-Chloro-6-fluoro-1-(2-phenethyl)-4-oxo-1,4-dihydroquinoline-3-carboxylic acid. A solution of ethyl 7-chloro-6-fluoro-1-(2-phenethyl)-4-oxo-1,4-dihydroquinoline-3-carboxylate (516 mg, 1.38 mmol) in 5.7 mL of an aq. 6 N HCl solution was placed in an oil bath at 113° C. for 3 h 40 m. Once at rt, the mixture was filtered and washed with water (2×10 mL) to give 466 mg (98%) of the acid as a solid.

e. 7-Chloro-1-(2-phenethyl)-6-(1,2,3,4-tetrahydronaphthyl-1-amino)-4-oxo-1,4-dihydroquinoline-3-carboxylic acid. Using the procedure described in Example 1, the title compound was isolated in 6% yield.

By using the method in Example 3, the following compounds were prepared:

7-Chloro-1-(benzyl)-6-(4-phenylbutyl-2-amino)-4-oxo-1,4-dihydroquinoline-3-carboxylic acid.

EXAMPLE 4

Modulation of [$^{35}$S]TBPS Binding in Rat Cortex by 7-chloro-1-ethyl-6-(1,2,3,4-tetrahydronaphthyl-1-amino)-4-oxo-1,4-dihydroquinoline-3-carboxylic acid The ability of 7-chloro-1-ethyl-6-(1,2,3,4-tetrahydronaphthyl-1-amino)-4-oxo-1,4-dihydroquinoline-3-carboxylic acid to inhibit the binding of [$^{35}$S]TBPS was determined according to the previously described method. The following compounds in Tables 1 and 2 were also tested for their ability to inhibit or enhance [$^{35}$S]TBPS binding to rat cortex.

TABLE 1

Inhibition or Enhancement of [$^{35}$S]TBPS binding by 6-Substituted Quinolones

| R group | % Inhibition or {Enhancement} of 2 nM TBPS in Rat Cortex at 10 μM |
|---|---|
| benzyl-NH | 0 |
| phenethyl-NH | 10 |
| 4-methoxyphenethyl-NH | 62 |
| 4-fluorophenethyl-NH | 26 |
| 4-chlorophenethyl-NH | 50 |
| 4-bromophenethyl-NH | 40 |
| α-methylphenethyl-NH | 65 (IC$_{50}$ = 4.0 μM) |
| 3-phenylpropyl-NH | 38 |
| 1,2,3,4-tetrahydronaphthyl-1-NH | 70 (IC$_{50}$ = 2.7 μM) |
| indan-1-yl-NH | 69 (IC$_{50}$ = 1.1 μM) |
| indan-2-yl-NH | 74 (IC$_{50}$ = 1.7 μM) |
| indol-3-yl-ethyl-NH | 29 |

TABLE 1-continued

Inhibition or Enhancement of [³⁵S]TBPS binding by 6-Substituted Quinolones

Core structure: 6-R, 7-Cl, 1-ethyl-4-oxo-quinoline-3-carboxylic acid

| R group | % Inhibition or {Enhancement} of 2 nM TBPS in Rat Cortex at 10 μM |
|---|---|
| PhCH₂CH₂CH₂CH₂NH– | 50 |
| 1-Naphthyl-CH₂-NH– | 35 |
| Ph₂CH-CH₂CH₂-NH– | 0 |
| 1-Naphthyl-CH(CH₃)-NH– | 65 |
| PhCH₂CH₂CH(CH₃)NH– | 84 (IC₅₀ = 2.0 μM) |
| 5-Methoxy-tryptamine-NH– | 26 |
| 3,4-Dimethoxyphenethyl-NH– | 12 |
| PhO-CH₂CH₂-NH– | 65 |
| PhNH-CH₂CH₂-NH– | 11 |
| n-C₈H₁₇-NH– | 0 |
| n-C₆H₁₃-CH(CH₃)-NH– | 31 |
| HO-CH₂CH₂-NH– | {17} IC₅₀ = 1.4 μM |
| 7-Methoxy-1,2,3,4-tetrahydronaphthyl-1-NH– | 66 |
| 2-Phenylcyclopropyl-NH– | 72 |
| 3-Methoxyphenethyl-NH– | 85 (IC₅₀ = 2.7 μM) |
| 6-Methyl-indan-1-yl-NH– | 59 |
| 2-Methoxyphenethyl-NH– | 32 |
| 3-Hydroxyphenethyl-NH– | |

TABLE 1-continued

Inhibition or Enhancement of [$^{35}$S]TBPS binding by 6-Substituted Quinolones

| Structure | % Inhibition or {Enhancement} of 2 nM TBPS in Rat Cortex at 10 μM |
|---|---|
| R, Cl, quinolone-COOH core with N-Et | |
| HO-C6H4-CH2CH2-NH2 | {32} |

TABLE 2

Inhibition of [$^{35}$S]TBPS binding to rat cortex by Quinolone Amides and Esters

| R group | % Inhibition or {Enhancement} of 2 nM TBPS in Rat Cortex at 10 μM |
|---|---|
| HN-propyl | 86 (IC$_{50}$ = 1.5 μM) |
| HN-CH2-(4-pyridyl) | 79 |
| HN-CH2CH2-phenyl | 65 |
| O-ethyl | IC$_{50}$ = 880 nM |

What is claimed is:

1. A compound having the Formula I:

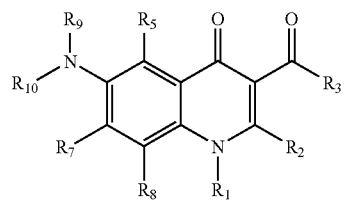

I or a pharmaceutically acceptable salt, prodrug or solvate thereof, wherein:

$R_1$ is selected from the group consisting of hydrogen; an optionally substituted alkyl, and aralkyl;

each $R_2$ is selected from the group consisting of hydrogen and optionally substituted alkyl;

each $R_3$ is selected from the group consisting of hydrogen, optionally substituted alkyl; a group $OR_{11}$ and $NR_{12}R_{13}$;

$R_5$, $R_7$ and $R_8$ are independently selected from the group consisting of hydrogen, an optionally substituted alkyl, and halogen;

$R_9$ and $R_{10}$ are independently selected from the group consisting of hydrogen, optionally substituted alkyl, aralkyl, cycloalkyl and cycloaralkyl; or $R_9$ and $R_{10}$ are taken together with the nitrogen atom to which they are attached to form a heterocyclic ring;

$R_{11}$ is selected from the group consisting of hydrogen, an alkali metal, a negative charge and optionally substituted alkyl;

$R_{12}$ and $R_{13}$ are independently selected from the group consisting of hydrogen, optionally substituted alkyl, aralkyl, aryl, cycloalkyl and cycloaralkyl; or $R_{12}$ and $R_{13}$ are taken together with the nitrogen atom to which they are attached to form a heterocyclic ring;

with the proviso that when $R_9$ and $R_{10}$ are taken together to form a piperazinyl ring, $R_7$ is Cl, $R_3$ is $OR_{11}$, $R_{11}$ is H, $R_5$ and $R_8$ are H, then $R_1$ is not Et; with the further proviso that when $R_9$ and $R_{10}$ taken together to form 4-methylpiperazine, $R_7$ is Cl, $R_3$ is $OR_{11}$, $R_{11}$ is H, and $R_5$ and $R_8$ are H, then $R_1$ is not Et; and with the further proviso that when $R_9$ and $R_{10}$ are taken together to form a morpholinyl ring, $R_1$, $R_2$, $R_5$, $R_7$, $R_8$ are H, $R_3$ is $NR_{12}R_{13}$ and either $R_{12}$ or $R_{13}$ is H, the other is not n-butyl.

2. A compound having the Formula II:

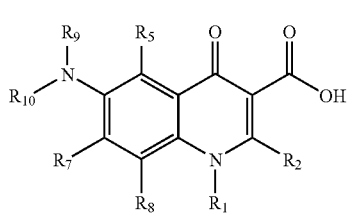

II or a pharmaceutically acceptable salt, prodrug or solvate thereof, wherein: $R_1$ is selected from the group consisting of hydrogen; an optionally substituted alkyl, and aralkyl; each $R_2$ is selected from the group consisting of hydrogen and optionally substituted alkyl; $R_5$, $R_7$ and $R_8$ are independently selected from the group consisting of hydrogen, an optionally substituted alkyl, and halogen; $R_9$ and $R_{10}$ are independently selected from the group consisting of optionally substituted alkyl, aralkyl, cycloalkyl and cycloaralkyl; or $R_9$ and $R_{10}$ are taken together with the nitrogen atom to which they are attached to form a heterocyclic ring;

with the proviso that when $R_9$ and $R_{10}$ are taken together to form piperazinyl ring, $R_7$ is Cl, $R_5$ and $R_8$ are H, then $R_1$ is not Et; and with the further proviso that when $R_9$ and $R_{10}$ are taken together to form 4-methylpiperazinyl, $R_7$ is Cl, and $R_5$ and $R_8$ are H, then $R_1$ is not Et.

3. A compound having the Formula III:

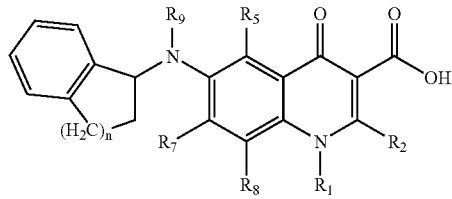

or a pharmaceutically acceptable salt, prodrug or solvate thereof, wherein: $R_1$, $R_2$, $R_5$, $R_7$, $R_8$, $R_9$ are as defined in claim 1; n is an integer 0, 1, 2, 3 or 4.

4. The compound of claim 3, wherein n is 2.

5. The compound of claim 3, wherein $R_1$ is alkyl, $R_2$, $R_5$ and $R_8$ are hydrogen and $R_7$ is halogen.

6. A compound of claim 1, wherein said compound is: 7-Chloro-1-ethyl-6-1,2,3,4-tetrahydronaphthyl-1-amino)-4-oxo-1,4-dihydroquinoline-3-carboxylic acid; (R)-7-Chloro-1-ethyl-6-(1,2,3,4-tetrahydronaphthyl-1-amino)-4-oxo-1,4-dihydroquinoline-3-carboxylic acid; (S)-7-Chloro-1-ethyl-6-(1,2,3,4-tetrahydronaphthyl-1-amino)-4-oxo-1,4-dihydroquinoline-3-carboxylic acid; 7-Chloro-1-ethyl-6-(1-aminoindanyl)-4-oxo-1,4-dihydroquinoline-3-carboxylic acid; 7-Chloro-1-ethyl-6-(2-aminoindanyl)-4-oxo-1,4-dihydroquinoline-3-carboxylic acid; 7-Chloro-1-ethyl-6-(benzylamino)-4-oxo-1,4-dihydroquinoline-3-carboxylic acid; 7-Chloro-1-ethyl-6-(phenethyl-2-amino)-4-oxo-1,4-dihydroquinoline-3-carboxylic acid; 7-Chloro-1-ethyl-6-[4-methoxy(phenethylamino)]-4-oxo-1,4-dihydroquinoline-3-carboxylic acid; 7-Chloro-1-ethyl-6-[3-methoxy(phenethylamino)]-4-oxo-1,4-dihydroquinoline-3-carboxylic acid; 7-Chloro-1-ethyl-6-[2-methoxy(phenethylamino)]-4-oxo-1,4-dihydroquinoline-3-carboxylic acid; 7-Chloro-1-ethyl-6-[4-bromo(phenethylamino)]-4-oxo-1,4-dihydroquinoline-3-carboxylic acid; 7-Chloro-1-ethyl-6-[4-chloro(phenethylamino)]-4-oxo-1,4-dihydroquinoline-3-carboxylic acid; 7-Chloro-1-ethyl-6-(3-phenylpropylamino)-4-oxo-1,4-dihydroquinoline-3-carboxylic acid; 7-Chloro-1-ethyl-6-(4-phenylbutylamino)-4-oxo-1,4-dihydroquinoline-3-carboxylic acid; 7-Chloro-1-ethyl-6-(4-phenylbutyl-2-amino)-4-oxo-1,4-dihydroquinoline-3-carboxylic acid; 7-Chloro-1-ethyl-6-(2-phenylpropylamino)-4-oxo-1,4-dihydroquinoline-3-carboxylic acid; 7-Chloro-1-ethyl-6-(2-phenoxyethylamino)-4-oxo-1,4-dihydroquinoline-3-carboxylic acid; or 7-Chloro-1-methyl-6-(1,2,3,4-tetrahydronaphthyl-1-amino)-4-oxo-1,4-dihydroquinoline-3-carboxylic acid; or a pharmaceutically acceptable salt, prodrug or solvate thereof.

7. A pharmaceutical composition, comprising the compound of Formula I:

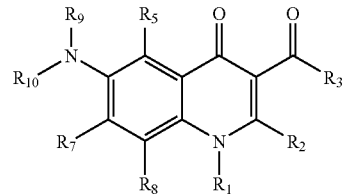

or a pharmaceutically acceptable salt, prodrug or solvate thereof, wherein: $R_1$ is selected from the group consisting of hydrogen; an optionally substituted alkyl, and aralkyl; each $R_2$ is selected from the group consisting of hydrogen and optionally substituted alkyl; each $R_3$ is selected from the group consisting of hydrogen, optionally substituted alkyl; a group $OR_{11}$ and $NR_{12}R_{13}$; $R_5$, $R_7$ and $R_8$ are independently selected from the group consisting of hydrogen, an optionally substituted alkyl, and halogen; $R_9$ and $R_{10}$ are independently selected from the group consisting of optionally substituted alkyl, aralkyl, cycloalkyl and cycloaralkyl; or $R_9$ and $R_{10}$ are taken together with the nitrogen atom to which they are attached to form a heterocyclic ring. $R_{11}$ is selected from the group consisting of hydrogen, an alkali metal, a negative charge and optionally substituted alkyl; $R_{12}$ and $R_{13}$ are independently selected from the group consisting of hydrogen, optionally substituted alkyl, aralkyl, aryl, cycloalkyl and cycloaralkyl; or $R_{12}$ and $R_{13}$ are taken together with the nitrogen atom to which they are attached to form a heterocyclic ring; and a pharmaceutically-acceptable carrier selected from the group consisting of excipients and auxiliaries;

with the proviso that when $R_9$ and $R_{10}$ are taken together to form piperazinyl ring, $R_7$ is Cl, $R_3$ is $OR_{11}$, $R_{11}$ is H, $R_5$ and $R_8$ are H, then $R_1$ is not Et; with the further proviso that when $R_9$ and $R_{10}$ are taken together to form 4-methylpiperazine, $R_7$ is Cl, $R_3$ is $OR_{11}$, $R_{11}$ is H, and $R_5$ and $R_8$ are H, then $R_1$ is not Et; and with the further proviso that when $R_9$ and $R_{10}$ are taken together to form a morpholinyl ring, $R_1$, $R_2$, $R_5$, $R_7$, $R_8$ are H, $R_3$ is $NR_{12}R_{13}$ and either $R_{12}$ or $R_{13}$ is H, the other is not n-butyl.

8. The composition of claim 7, wherein the compound comprises a compound having the Formula I:

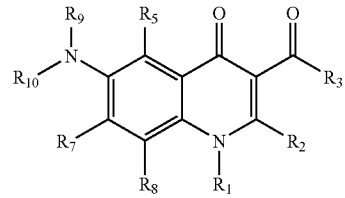

or a pharmaceutically acceptable salt, prodrug or solvate thereof, wherein: $R_1$ is selected from the group consisting of hydrogen; an optionally substituted alkyl, and aralkyl; each $R_2$ is selected from the group consisting of hydrogen and optionally substituted alkyl; each $R_3$ is selected from the group consisting of hydrogen, optionally substituted alkyl; a group $OR_{11}$ and $NR_{12}R_{13}$; $R_5$, $R_7$ and $R_8$ are independently selected from the group consisting of hydrogen, an optionally substituted alkyl, and halogen; $R_9$ and $R_{10}$ are independently selected from the group consisting of hydrogen, optionally substituted alkyl, aralkyl, cycloalkyl and cycloaralkyl; or $R_9$ and $R_{10}$ are taken together with the nitrogen atom to which they are attached to form a heterocyclic ring; $R_{11}$ is selected from the group consisting of hydrogen, an alkali metal, a negative charge and optionally substituted alkyl; $R_{12}$ and $R_{13}$ are independently selected from the group consisting of hydrogen, optionally substituted alkyl, aralkyl, aryl, cycloalkyl and cycloaralkyl; or $R_2$ and $R_3$ are taken together with the nitrogen atom to which they are attached to form a heterocyclic ring;

with the proviso that when $R_9$ and $R_{10}$ are taken together to form a piperazinyl ring, $R_7$ is Cl, $R_3$ is $OR_{11}$, $R_{11}$ is H, $R_5$ and $R_8$ are H, then $R_1$ is not Et; with the further proviso that when $R_9$ and $R_{10}$ are taken together to form 4-methylpiperazinyl, $R_7$ is Cl, $R_3$ is $OR_{11}$, $R_{11}$ is H, and $R_5$ and $R_8$ are H, then $R_1$ is not Et; and with the further proviso that when $R_9$ and $R_{10}$ are taken together to form a morpholinyl ring, $R_1$, $R_2$, $R_5$, $R_7$, $R_8$ are H, $R_3$ is $NR_{12}R_{13}$ and either $R_{12}$ or $R_{13}$ is H, the other is not n-butyl.

9. The composition of claim 7, wherein the compound comprises a compound having the Formula II:

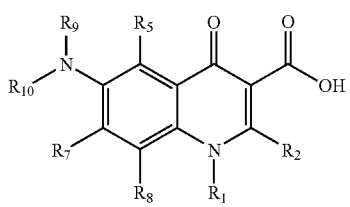

II or a pharmaceutically acceptable salt, prodrug or solvate thereof, wherein: $R_1$ is selected from the group consisting of hydrogen; an optionally substituted alkyl, and aralkyl; each $R_2$ is selected from the group consisting of hydrogen and optionally substituted alkyl; $R_5$, $R_7$ and $R_8$ are independently selected from the group consisting of hydrogen, an optionally substituted alkyl, and halogen; $R_9$ and $R_{10}$ are independently selected from the group consisting of optionally substituted alkyl, aralkyl, cycloalkyl and cycloaralkyl; or $R_9$ and $R_{10}$ are taken together with the nitrogen atom to which they are attached to form a heterocyclic ring;

with the proviso that when $R_9$ and $R_{10}$ are taken together to form a piperazinyl, $R_7$ is Cl, $R_5$ and $R_8$ are H, then $R_1$ is not Et; and with the further proviso that when $R_9$ and $R_{10}$ are taken together to form 4-methylpiperazinyl, $R_7$ is Cl, and $R_5$ and $R_8$ are H, then $R_1$ is not Et.

10. The composition of claim 7, wherein the compound comprises a compound having the Formula III: or a pharmaceutically acceptable salt, prodrug or solvate thereof, wherein: $R_1$, $R_2$, $R_5$, $R_7$, $R_8$, $R_9$ are as defined in claim 1; n is an integer 0, 1, 2, 3 or 4.

11. The composition of claim 10, wherein n is 2.

12. The composition of claim 10, wherein $R_1$ is alkyl, $R_2$, $R_5$ and $R_8$ are hydrogen and $R_7$ is halogen.

13. The composition of claim 7, wherein the compound is: 7-Chloro-1-ethyl-6-(1,2,3,4-tetrahydronaphthyl-1-amino)-4-oxo-1,4-dihydroquinoline-3-carboxylic acid; (R)-7-Chloro-1-ethyl-6-(1,2,3,4-tetrahydronaphthyl-1-amino)-4-oxo-1,4-dihydroquinoline-3-carboxylic acid; (S)-7-Chloro-1-ethyl-6-(1,2,3,4-tetrahydronaphthyl-1-amino)-4-oxo-1,4-dihydroquinoline-3-carboxylic acid; 7-Chloro-1-ethyl-6-(1-aminoindanyl)-4-oxo-1,4-dihydroquinoline-3-carboxylic acid; 7-Chloro-1-ethyl-6-(2-aminoindanyl)-4-oxo-1,4-dihydroquinoline-3-carboxylic acid; 7-Chloro-1-ethyl-6-(benzylamino)-4-oxo-1,4-dihydroquinoline-3-carboxylic acid; 7-Chloro-1-ethyl-6-(phenethyl-2-amino)-4-oxo-1,4-dihydroquinoline-3-carboxylic acid; 7-Chloro-1-ethyl-6-[4-methoxy(phenethylamino)]-4-oxo-1,4-dihydroquinoline-3-carboxylic acid; 7-Chloro-1-ethyl-6-[3-methoxy(phenethylamino)]-4-oxo-1,4-dihydroquinoline-3-carboxylic acid; 7-Chloro-1-ethyl-6-[2-methoxy(phenethylamino)]-4-oxo-1,4-dihydroquinoline-3-carboxylic acid; 7-Chloro-1-ethyl-6-[4-bromo(phenethylamino)]-4-oxo-1,4-dihydroquinoline-3-carboxylic acid; 7-Chloro-1-ethyl-6-[4-chloro(phenethylamino)]-4-oxo-1,4-dihydroquinoline-3-carboxylic acid; 7-Chloro-1-ethyl-6-(3-phenylpropylamino)-4-oxo-1,4-dihydroquinoline-3-carboxylic acid; 7-Chloro-1-ethyl-6-(4-phenylbutylamino)-4-oxo-1,4-dihydroquinoline-3-carboxylic acid; 7-Chloro-1-ethyl-6-(4-phenylbutyl-2-amino)-4-oxo-1,4-dihydroquinoline-3-carboxylic acid; 7-Chloro-1-ethyl-6-(2-phenylpropylamino)-4-oxo-1,4-dihydroquinoline-3-carboxylic acid; 7-Chloro-1-ethyl-6-(2-phenoxyethylamino)-4-oxo-1,4-dihydroquinoline-3-carboxylic acid; or 7-Chloro-1-methyl-6-(1,2,3,4-tetrahydronaphthyl-1-amino)-4-oxo-1,4-dihydroquinoline-3-carboxylic acid or a pharmaceutically acceptable salt, prodrug or solvate thereof.

14. The method of claim 9, wherein the compound is: 7-Chloro-1-ethyl-6-(1,2,3,4-tetrahydronaphthyl-1-amino)-4-oxo-1,4-dihydroquinoline-3-carboxylic acid; (R)-7-Chloro-1-ethyl-6-(1,2,3,4-tetrahydronaphthyl-1-amino)-4-oxo-1,4-dihydroquinoline-3-carboxylic acid; (S)-7-Chloro-1-ethyl-6-(1,2,3,4-tetrahydronaphthyl-1-amino)-4-oxo-1,4-dihydroquinoline-3-carboxylic acid; 7-Chloro-1-ethyl-6-(1-aminoindanyl)-4-oxo-1,4-dihydroquinoline-3-carboxylic acid; 7-Chloro-1-ethyl-6-(2-aminoindanyl)-4-oxo-1,4-dihydroquinoline-3-carboxylic acid; 7-Chloro-1-ethyl-6-(benzylamino)-4-oxo-1,4-dihydroquinoline-3-carboxylic acid; 7-Chloro-1-ethyl-6-(phenethyl-2-amino)-4-oxo-1,4-dihydroquinoline-3-carboxylic acid; 7-Chloro-1-ethyl-6-[4-methoxy(phenethylamino)]-4-oxo-1,4-dihydroquinoline-3-carboxylic acid; 7-Chloro-1-ethyl-6-[3-methoxy(phenethylamino)]-4-oxo-1,4-dihydroquinoline--3-carboxylic acid; 7-Chloro-1-ethyl-6-[2-methoxy(phenethylamino)]-4-oxo-1,4-dihydroquinoline-3-carboxylic acid; 7-Chloro-1-ethyl-6-[4-bromo(phenethylamino)]-4-oxo-1,4-dihydroquinoline-3-carboxylic acid; 7-Chloro-1-ethyl-6-[4-chloro(phenethylamino)]-4-oxo-1,4-dihydroquinoline-3-carboxylic acid; 7-Chloro-1-ethyl-6-(3-phenylpropylamino)-4-oxo-1,4-dihydroquinoline-3-carboxylic acid; 7-Chloro-1-ethyl-6-(4-phenylbutylamino)-4-oxo-1,4-dihydroquinoline-3-carboxylic acid; 7-Chloro-1-ethyl-6-(4-phenylbutyl-2-amino)-4-oxo-1,4-dihydroquinoline-3-carboxylic acid; 7-Chloro-1-ethyl-6-(2-phenylpropylamino)-4-oxo-1,4-dihydroquinoline-3-carboxylic acid; 7-Chloro-1-ethyl-6-(2-phenoxyethylamino)-4-oxo-1,4-dihydroquinoline-3-carboxylic acid; or 7-Chloro-1-methyl-6-(1,2,3,4-tetrahydronaphthyl-1-amino)-4-oxo-1,4-dihydroquinoline-3-carboxylic acid or a pharmaceutically acceptable salt, prodrug or solvate thereof.

* * * * *

UNITED STATES PATENT AND TRADEMARK OFFICE
CERTIFICATE OF CORRECTION

PATENT NO.         : 7,355,047 B2
APPLICATION NO.    : 10/514808
DATED              : April 8, 2008
INVENTOR(S)        : Johnstone et al.

It is certified that error appears in the above-identified patent and that said Letters Patent is hereby corrected as shown below:

IN THE CLAIMS:

Please replace Claim 14 as follows:

14. The composition of claim 9, wherein the compound is: 7-Chloro-1-ethyl-6-(1,2,3,4-tetrahydronaphthyl-1-amino)-4-oxo-1,4-dihydroquinoline-3-carboxylic acid; (R)-7-Chloro-1-ethyl-6-(1,2,3,4-tetrahydronaphthyl-1-amino)-4-oxo-1,4-dihydroquinoline-3-carboxylic acid; (S)-7-Chloro-1-ethyl-6-(1,2,3,4-tetrahydronaphthyl-1-amino)-4-oxo-1,4-dihydroquinoline-3-carboxylic acid; 7-Chloro-1-ethyl-6-(1-aminoindanyl)-4-oxo-1,4-dihydroquinoline-3-carboxylic acid; 7-Chloro-1-ethyl-6-(2-aminoindanyl)-4-oxo-1,4-dihydroquinoline-3-carboxylic acid; 7-Chloro-1-ethyl-6-(benzylamino)-4-oxo-1,4-dihydroquinoline-3-carboxylic acid; 7-Chloro-1-ethyl-6-(phenethyl-2-amino)-4-oxo-1,4-dihydroquinoline-3- -carboxylic acid; 7-Chloro-1-ethyl-6-[4-methoxy(phenethylamino)]-4-oxo-1,4-dihydroquinoline-3-carboxylic acid; 7-Chloro-1-ethyl-6-[3-methoxy(phenethylamino)]-4-oxo-1,4-dihydroquinoline-3-carboxylic acid; 7-Chloro-1-ethyl-6-[2-methoxy(phenethylamino)]-4-oxo-1,4-dihydroquinoline-3-carboxylic acid; 7-Chloro-1-ethyl-6-[4-bromo(phenethylamino)]-4-oxo-1,4-dihydroquinoline-3-carboxylic acid; 7-Chloro-1-ethyl-6-[4-chloro(phenethylamino)]-4-oxo-1,4-dihydroquinoline-3-carboxylic acid; 7-Chloro-1-ethyl-6-(3-phenylpropylamino)-4-oxo-1,4-dihydroquinoline-3-carboxylic acid; 7-Chloro-1-ethyl-6-(4-phenylbutylamino)-4-oxo-1,4-dihydroquinoline-3-carboxylic acid; 7-Chloro-1-ethyl-6-(4-phenylbutyl-2-amino)-4-oxo-1,4-dihydroquinoline-3-carboxylic acid; 7-Chloro-1-ethyl-6-(2-phenylpropylamino)-4-oxo-1,4-dihydroquinoline-3-carboxylic acid; 7-Chloro-1-ethyl-6-(2-phenoxyethylamino)-4-oxo-1,4-dihydroquinoline-3-carboxylic acid; or 7-Chloro-1-methyl-6-(1,2,3,4-tetrahydronaphthyl-1-amino)-4-oxo-1,4-dihydroquinoline-3-carboxylic acid or a pharmaceutically acceptable salt, prodrug or solvate thereof.

Signed and Sealed this

First Day of July, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,355,047 B2 | |
| APPLICATION NO. | : 10/514808 | |
| DATED | : April 8, 2008 | |
| INVENTOR(S) | : Johnstone et al. | |

It is certified that error appears in the above-identified patent and that said Letters Patent is hereby corrected as shown below:

IN THE CLAIMS:

Column 6, lines 33-65,

Please replace Claim 14 as follows:
14. The composition of claim 9, wherein the compound is: 7-Chloro-1-ethyl-6-(1,2,3,4-tetrahydronaphthyl-1-amino)-4-oxo-1,4-dihydroquinoline-3-carboxylic acid; (R)-7-Chloro-1-ethyl-6-(1,2,3,4-tetrahydronaphthyl-1-amino)-4-oxo-1,4-dihydroquinoline-3-carboxylic acid; (S)-7-Chloro-1-ethyl-6-(1,2,3,4-tetrahydronaphthyl-1-amino)-4-oxo-1,4-dihydroquinoline-3-carboxylic acid; 7-Chloro-1-ethyl-6-(1-aminoindanyl)-4-oxo-1,4-dihydroquinoline-3-carboxylic acid; 7-Chloro-1-ethyl-6-(2-aminoindanyl)-4-oxo-1,4-dihydroquinoline-3-carboxylic acid; 7-Chloro-1-ethyl-6-(benzylamino)-4-oxo-1,4-dihydroquinoline-3-carboxylic acid; 7-Chloro-1-ethyl-6-(phenethyl-2-amino)-4-oxo-1,4-dihydroquinoline-3- -carboxylic acid; 7-Chloro-1-ethyl-6-[4-methoxy(phenethylamino)]-4-oxo-1,4-dihydroquinoline-3-carboxylic acid; 7-Chloro-1-ethyl-6-[3-methoxy(phenethylamino)]-4-oxo-1,4-dihydroquinoline-3-carboxylic acid; 7-Chloro-1-ethyl-6-[2-methoxy(phenethylamino)]-4-oxo-1,4-dihydroquinoline-3-carboxylic acid; 7-Chloro-1-ethyl-6-[4-bromo(phenethylamino)]-4-oxo-1,4-dihydroquinoline-3-carboxylic acid; 7-Chloro-1-ethyl-6-[4-chloro(phenethylamino)]-4-oxo-1,4-dihydroquinoline-3-carboxylic acid; 7-Chloro-1-ethyl-6-(3-phenylpropylamino)-4-oxo-1,4-dihydroquinoline-3-carboxylic acid; 7-Chloro-1-ethyl-6-(4-phenylbutylamino)-4-oxo-1,4-dihydroquinoline-3-carboxylic acid; 7-Chloro-1-ethyl-6-(4-phenylbutyl-2-amino)-4-oxo-1,4-dihydroquinoline-3-carboxylic acid; 7-Chloro-1-ethyl-6-(2-phenylpropylamino)-4-oxo-1,4-dihydroquinoline-3-carboxylic acid; 7-Chloro-1-ethyl-6-(2-phenoxyethylamino)-4-oxo-1,4-dihydroquinoline-3-carboxylic acid;

UNITED STATES PATENT AND TRADEMARK OFFICE
CERTIFICATE OF CORRECTION

PATENT NO. : 7,355,047 B2
APPLICATION NO. : 10/514808
DATED : April 8, 2008
INVENTOR(S) : Johnstone et al.

It is certified that error appears in the above-identified patent and that said Letters Patent is hereby corrected as shown below:

or 7-Chloro-1-methyl-6-(1,2,3,4-tetrahydronaphthyl-1-amino)-4-oxo-1,4-dihydroquinoline-3-carboxylic acid or a pharmaceutically acceptable salt, prodrug or solvate thereof.

This certificate supersedes the Certificate of Correction issued July 1, 2008.

Signed and Sealed this

Twenty-second Day of July, 2008

JON W. DUDAS
*Director of the United States Patent and Trademark Office*